(12) United States Patent
Schotzko et al.

(10) Patent No.: US 10,813,740 B2
(45) Date of Patent: Oct. 27, 2020

(54) EMBOLIC PROTECTION DEVICE

(71) Applicant: MEDTRONIC, INC., Minneapolis, MN (US)

(72) Inventors: Elizabeth Schotzko, Mounds View, MN (US); Joel Racchini, Mounds View, MN (US); Jeffrey Sandstrom, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 289 days.

(21) Appl. No.: 16/011,057

(22) Filed: Jun. 18, 2018

(65) Prior Publication Data
US 2018/0360588 A1 Dec. 20, 2018

Related U.S. Application Data

(62) Division of application No. 14/937,668, filed on Nov. 10, 2015, now Pat. No. 9,999,492, which is a division of application No. 13/777,141, filed on Feb. 26, 2013, now Pat. No. 9,211,179.

(51) Int. Cl.
*A61F 2/01* (2006.01)

(52) U.S. Cl.
CPC .............. *A61F 2/013* (2013.01); *A61F 2/011* (2020.05); *A61F 2210/009* (2013.01)

(58) Field of Classification Search
CPC .......... A61F 2002/011; A61F 2210/009; A61F 2/013; A61F 2002/016; A61F 2/01
See application file for complete search history.

(56) References Cited

U.S. PATENT DOCUMENTS

| | | | |
|---|---|---|---|
| 6,346,116 B1 | 2/2002 | Brooks et al. | |
| 6,602,271 B2 | 8/2003 | Adams et al. | |
| 6,676,694 B1 | 1/2004 | Weiss | |
| 6,994,718 B2 | 2/2006 | Groothuis et al. | |
| 2002/0083639 A1 | 6/2002 | Broome et al. | |
| 2003/0171770 A1 | 9/2003 | Kusleika et al. | |
| 2004/0153447 A1 | 8/2004 | Clubb et al. | |
| 2004/0215167 A1 | 10/2004 | Belson | |
| 2005/0096691 A1 | 5/2005 | Groothuis et al. | |

(Continued)

FOREIGN PATENT DOCUMENTS

| | | |
|---|---|---|
| WO | 2001008595 A1 | 2/2001 |
| WO | 2001035857 A1 | 2/2001 |

(Continued)

*Primary Examiner* — Katherine M Shi
(74) *Attorney, Agent, or Firm* — Medler Ferro Woodhouse & Mills PLLC

(57) ABSTRACT

An embolic protection device includes a shaft, a first magnet fixedly coupled to a distal portion of the shaft, a second magnet slidingly coupled to the shaft proximal to the first magnet, and a filter including a distal portion coupled to the first magnet and a proximal portion coupled to the second magnet. The first and second magnets are magnetically attracted to each other such that in a radially compressed configuration of the filter, the second magnet is spaced from the first magnet a first distance, and in a radially expanded configuration of the filter, the second magnet slides towards the first magnet such that the second magnet is spaced a second distance from the first magnet, wherein the second distance is smaller than the first distance.

11 Claims, 18 Drawing Sheets

(56) References Cited

U.S. PATENT DOCUMENTS

| | | |
|---|---|---|
| 2005/0124876 A1 | 6/2005 | Douk et al. |
| 2006/0155322 A1 | 7/2006 | Sater et al. |
| 2006/0282113 A1 | 12/2006 | Sater |
| 2007/0073332 A1 | 3/2007 | Miller et al. |
| 2007/0073333 A1 | 3/2007 | Coyle |
| 2007/0112371 A1 | 5/2007 | Cangialosi et al. |
| 2007/0299466 A1 | 12/2007 | Sachar et al. |
| 2008/0103522 A1 | 5/2008 | Steingisser et al. |
| 2008/0255606 A1 | 10/2008 | Mitra et al. |
| 2009/0287293 A1* | 11/2009 | Mailhot, Jr. ............. A61F 2/91 623/1.15 |
| 2010/0198211 A1* | 8/2010 | Kassab .......... A61B 17/320758 606/32 |
| 2014/0163603 A1 | 6/2014 | Zajarias |

FOREIGN PATENT DOCUMENTS

| | | |
|---|---|---|
| WO | 2001089413 A2 | 11/2001 |
| WO | 2002072172 A2 | 9/2002 |
| WO | 2003075997 A1 | 9/2003 |
| WO | 2005051236 A2 | 6/2005 |
| WO | 2010082189 A1 | 7/2010 |

* cited by examiner

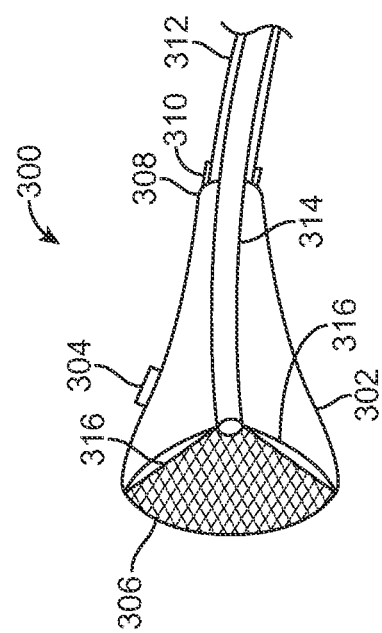
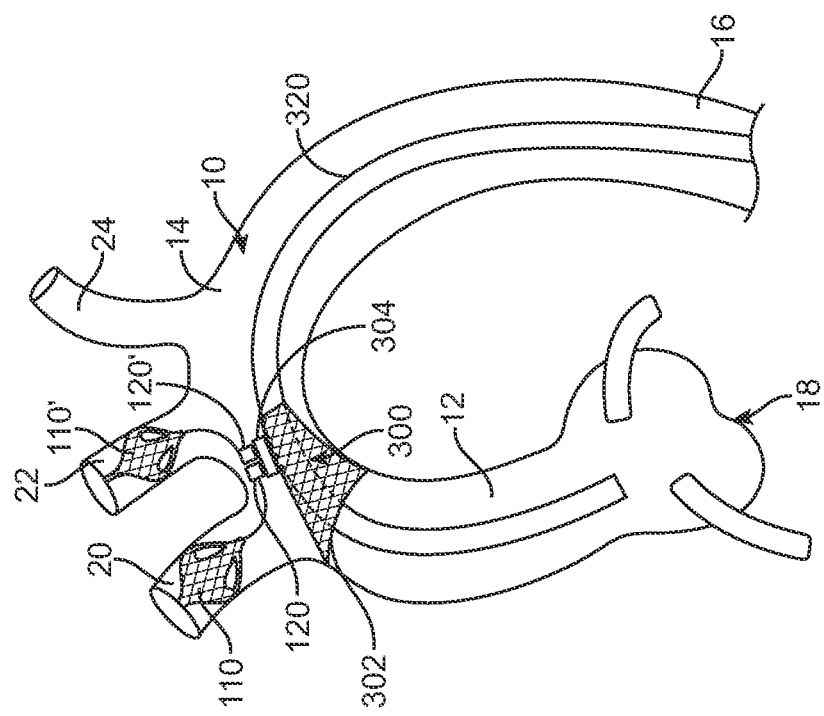

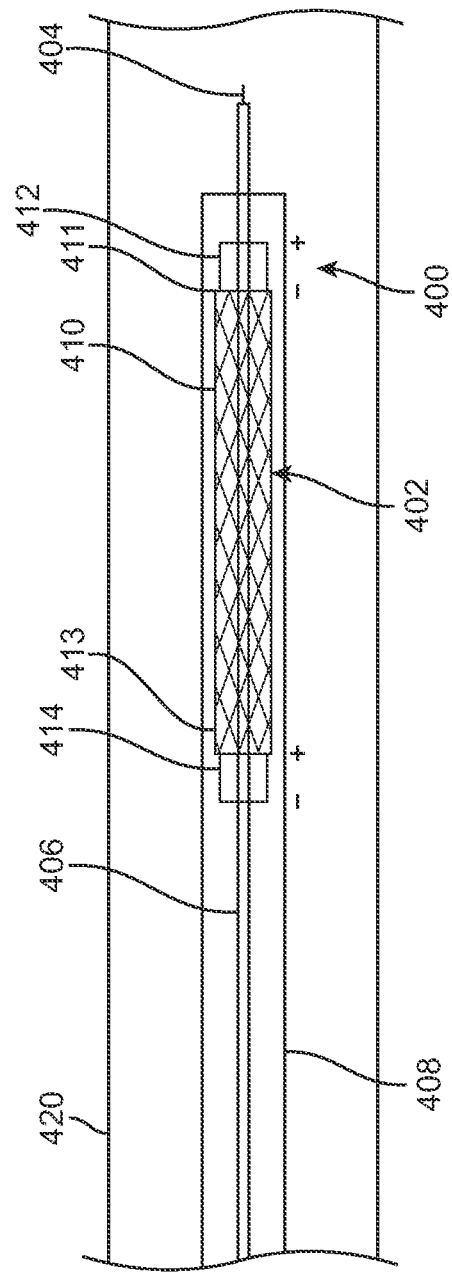
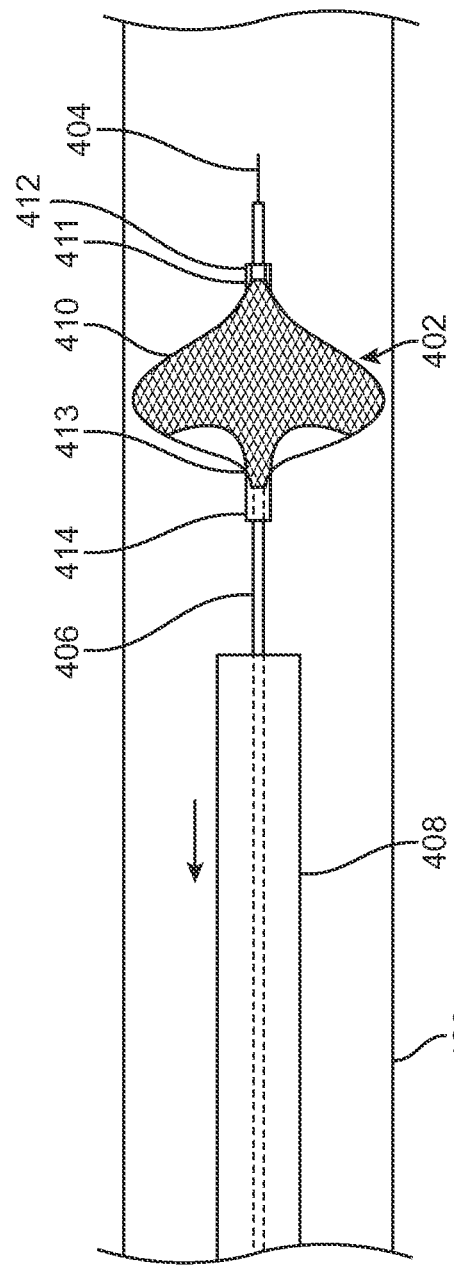
FIG. 23
FIG. 24

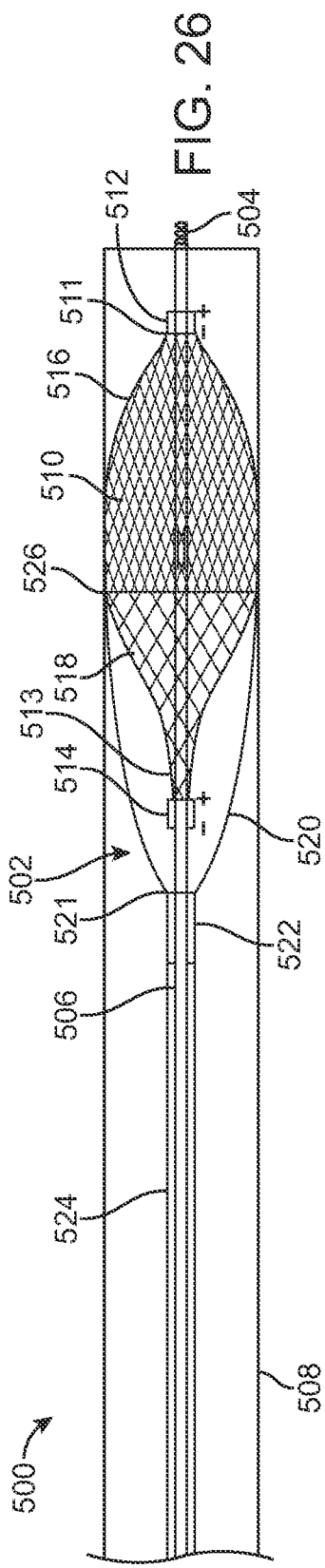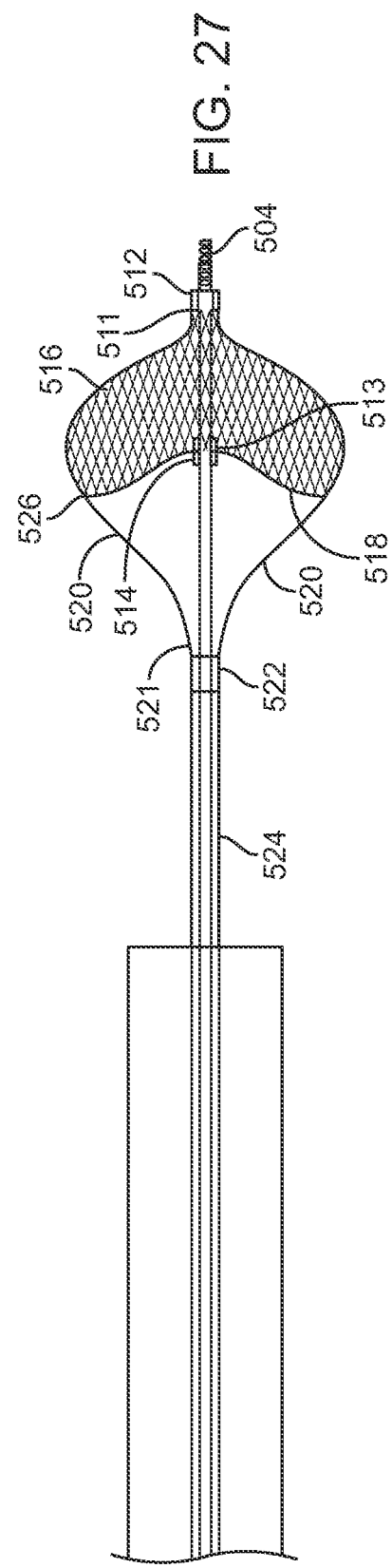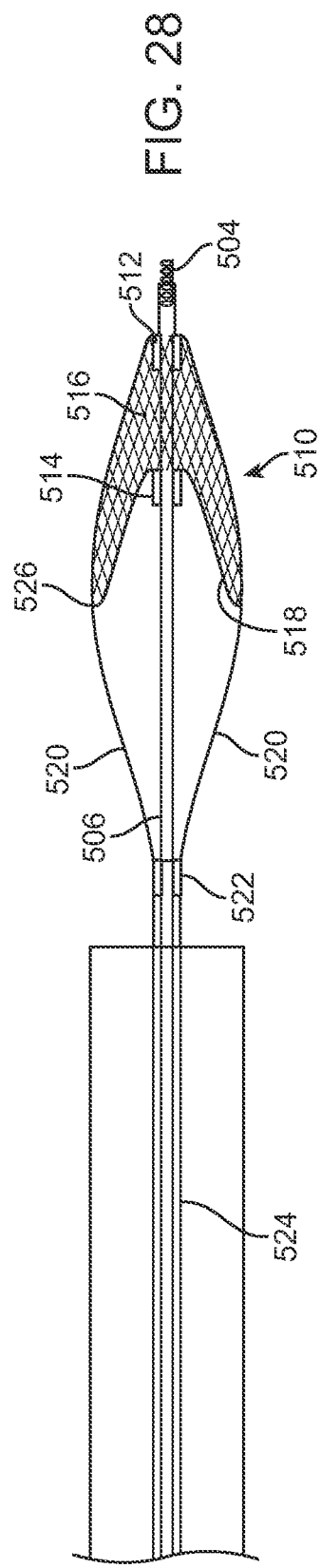

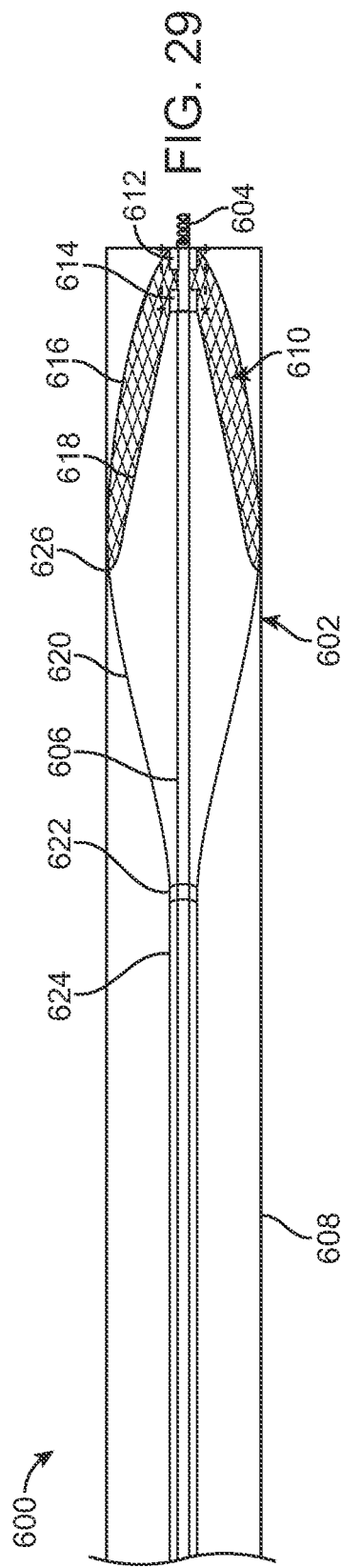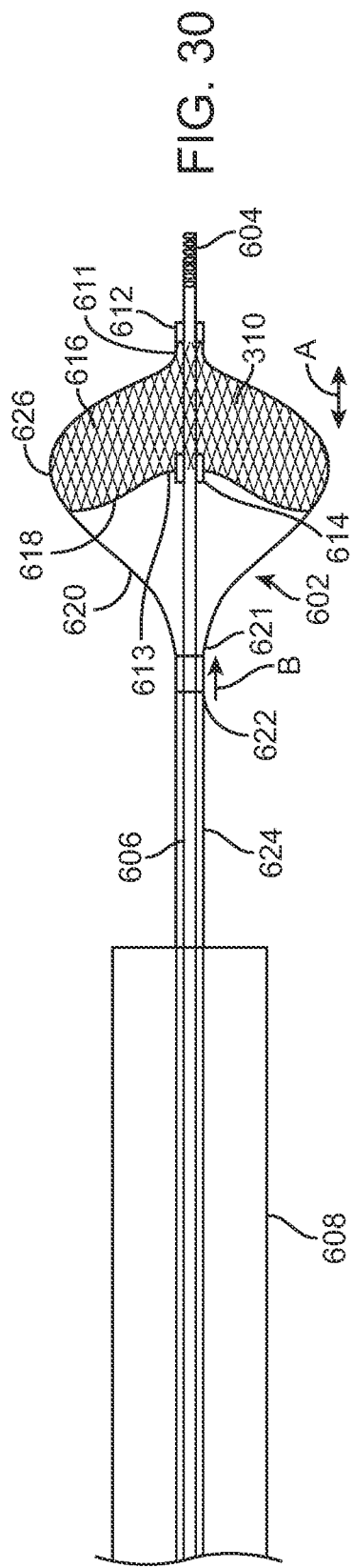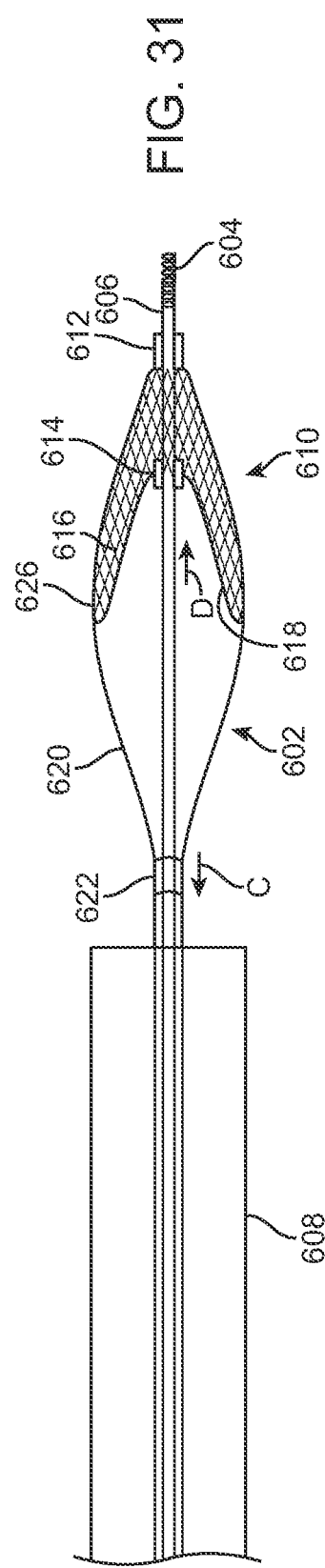

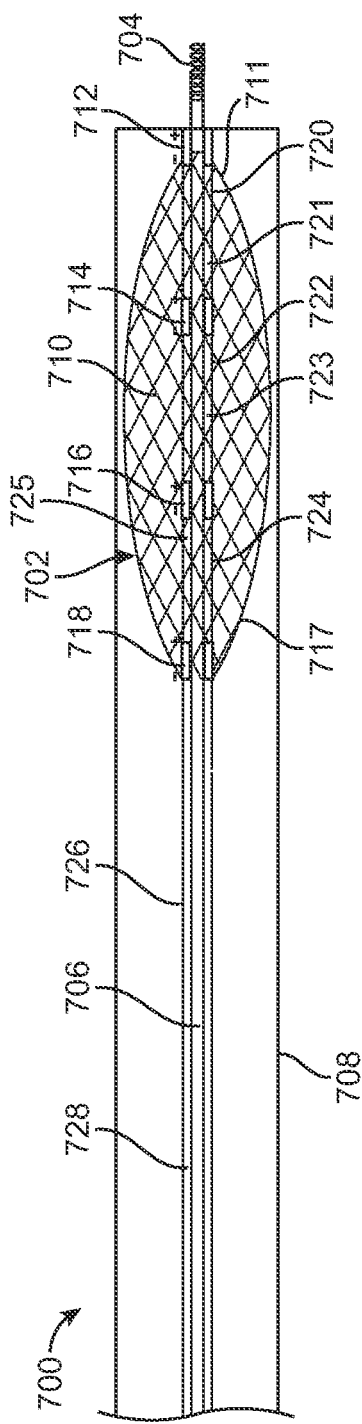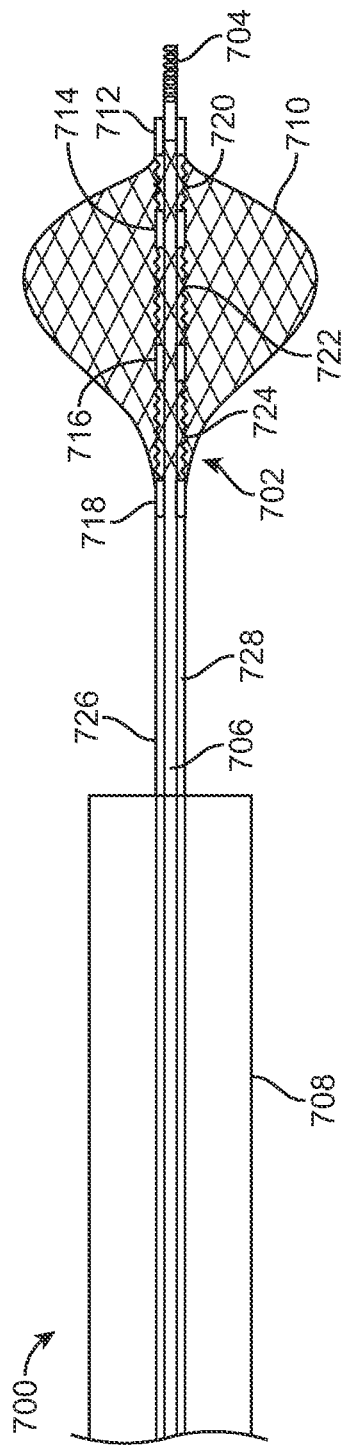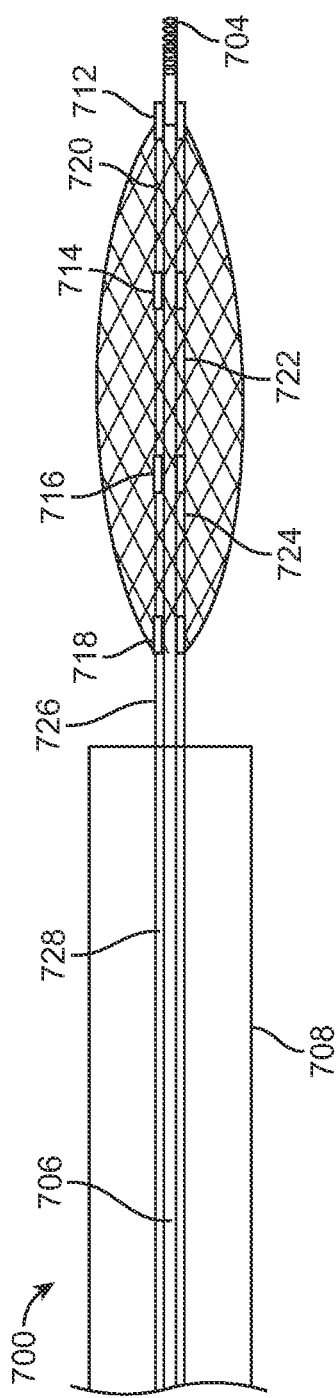

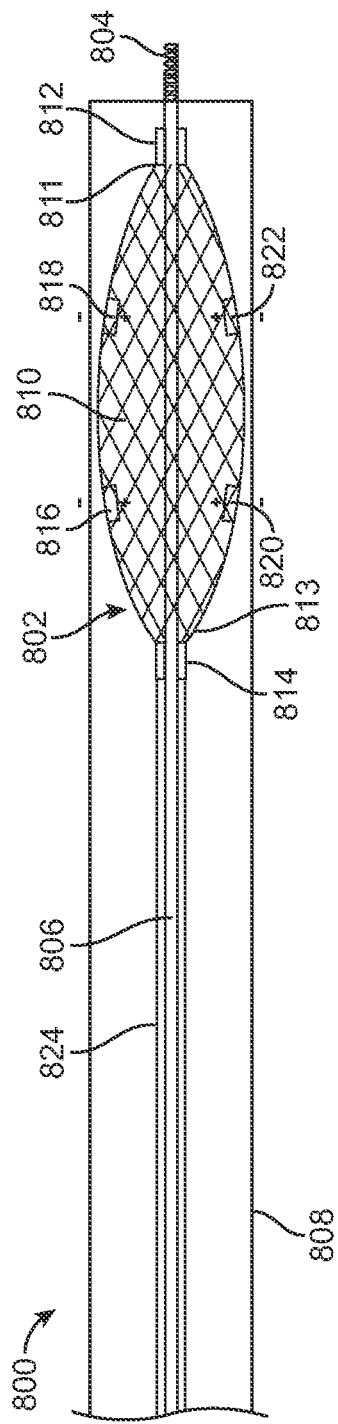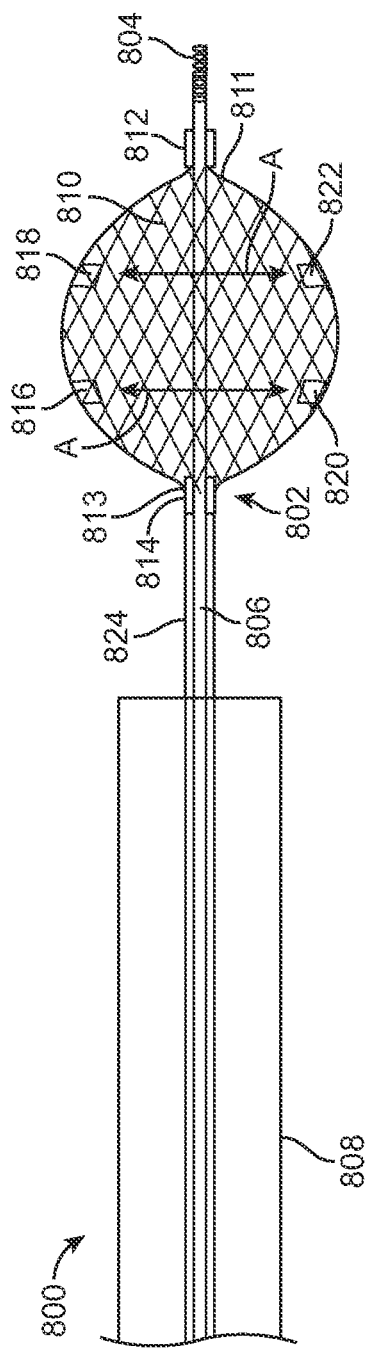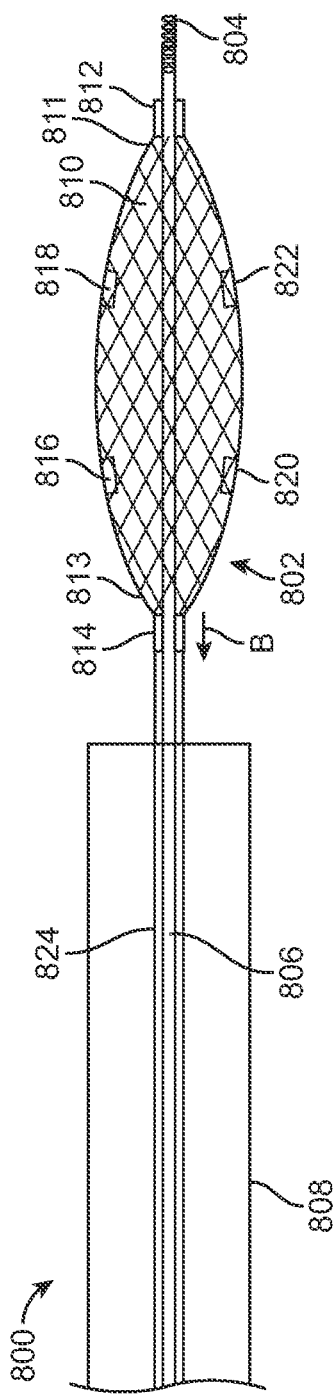

EMBOLIC PROTECTION DEVICE

CROSS-REFERENCE TO RELATED APPLICATIONS

The present application is a Division of U.S. patent application Ser. No. 14/937,668 filed Nov. 10, 2015, now U.S. Pat. No. 9,999,492, issued Jun. 19, 2018, which is a Division of U.S. patent application Ser. No. 13/777,141, filed Feb. 26, 2013, now U.S. Pat. No. 9,211,179, issued Dec. 15, 2015, the contents of both of which are incorporated herein by reference in their entirety.

FIELD OF THE INVENTION

The invention relates generally to intraluminal distal protection devices for capturing particulate in the vessels of a patient. More particularly, the invention relates to filter devices for capturing emboli in a blood vessel during an interventional vascular procedure, the filter having magnets to tether filters together or to open and close the filters.

BACKGROUND

Catheters have long been used for the treatment of diseases of the cardiovascular system, such as treatment or removal of stenosis. For example, in a percutaneous transluminal coronary angioplasty (PTCA) procedure, a catheter is used to transport a balloon into a patient's cardiovascular system, position the balloon at a desired treatment location, inflate the balloon, and remove the balloon from the patient. Another example of a common catheter-based treatment is the placement of an intravascular stent in the body on a permanent or semi-permanent basis to support weakened or diseased vascular walls, or to avoid closure, re-closure or rupture thereof. More recently, catheters have been used for replacement of heart valves, in particular, the aortic valve in a procedure sometimes known as transcatheter aortic valve implantation ("TAVI") or transcatheter aortic valve replacement ("TAVR").

These non-surgical interventional procedures often avoid the necessity of major surgical operations. However, one common problem associated with these procedures is the potential release of embolic debris into the bloodstream that can occlude distal vasculature and cause significant health problems to the patient.

Medical devices have been developed to attempt to deal with the problem created when debris or fragments enter the circulatory system during vessel treatment. One technique includes the placement of a filter or trap downstream from the treatment site to capture embolic debris before it reaches the smaller blood vessels downstream. The placement of a filter in the patient's vasculature during treatment of the vascular lesion can collect embolic debris in the bloodstream.

It is known to attach an expandable filter to a distal end of a guidewire or guidewire-like member that allows the filtering device to be placed in the patient's vasculature. The guidewire allows the physician to steer the filter to a location downstream from the area of treatment. Once the guidewire is in proper position in the vasculature, the embolic filter can be deployed to capture embolic debris. Some embolic filtering devices utilize a restraining sheath to maintain the expandable filter in its collapsed configuration. Once the proximal end of the restraining sheath is retracted by the physician, the expandable filter will transform into its fully expanded configuration in apposition with the vessel wall. The restraining sheath can then be removed from the guidewire allowing the guidewire to be used by the physician to deliver interventional devices, such as a balloon angioplasty catheter or a stent delivery catheter, into the area of treatment. After the interventional procedure is completed, a recovery sheath can be delivered over the guidewire using over-the-wire techniques to collapse the expanded filter (with the trapped embolic debris) for removal from the patient's vasculature. Both the delivery sheath and recovery sheath should be relatively flexible to track over the guidewire and to avoid straightening the body vessel once in place.

Another distal protection device known in the art includes a filter mounted on a distal portion of a hollow guidewire or tube. A moveable core wire is used to open and close the filter. The filter is coupled at a proximal end to the tube and at a distal end to the core wire. Pulling on the core wire while pushing on the tube draws the ends of the filter toward each other, causing the filter framework between the ends to expand outward into contact with the vessel wall. Filter mesh material is mounted to the filter framework. To collapse the filter, the procedure is reversed, i.e., pulling the tube proximally while pushing the core wire distally to force the filter ends apart. A sheath catheter may be used as a retrieval catheter at the end of the interventional procedure to reduce the profile of the "push-pull" filter, as due to the embolic particles collected, the filter may still be in a somewhat expanded state. The retrieval catheter may be used to further collapse the filter and/or smooth the profile thereof, so that the filter guidewire may pass through the treatment area without disturbing any stents or otherwise interfering with the treated vessel.

TAVR procedures present difficulties not encountered in other procedures. For example, three branch vessels extend from the aortic arch towards the upper body. In particular, the right common carotid artery, which branches from the brachiocephalic artery, and the left common carotid artery deliver blood to the brain. Emboli entering these arteries pose an increased risk of stroke by blocking the smaller blood vessels in the brain. Further, many TAVR procedures provide access through the femoral artery, up through abdominal aortic, the aortic arch, and then crossing the aortic valve. Filter devices to be deployed to protect the carotid in many cases need to be delivered through a different pathway so that the delivery device for the filter does not interfere with the delivery device for the replacement valve. This requires an additional access site, such as the brachial artery.

Accordingly, there is a need for improved embolic protection devices for TAVR procedures.

SUMMARY OF THE INVENTION

Embodiments hereof relate to an embolic protection device including a first filter configured to be disposed in a first vessel and a second filter configured to be disposed in a second vessel. A first tether extends from a proximal end of the first filter and a first magnet is coupled to the first tether. A second tether extends from a proximal end of the second filter and a second magnet is coupled to the second tether. The device is configured such that when the first filter is disposed in the first vessel and the second filter is disposed in the second vessel, the first magnet and the second magnet are magnetically coupled to each other to couple the first tether to the second tether.

Embodiments hereof also relate to an embolic protection device including a shaft, a first magnet fixedly coupled to a distal portion of the shaft, a second magnet slidingly coupled to the shaft proximal to the first magnet, and a filter including a distal portion coupled to the first magnet and a proximal portion coupled to the second magnet. The first and second magnets are magnetically attracted to each other such that in a radially compressed configuration of the filter, the second magnet is spaced from the first magnet a first distance, and in a radially expanded configuration of the filter, the second magnet slides towards the first magnet such that the second magnet is spaced a second distance from the first magnet, wherein the second distance is smaller than the first distance.

Embodiments hereof also relate to an embolic protection system including an inner shaft and a filter coupled to the inner shaft. The filter includes a first filter portion and a second filter portion. A first magnet is fixedly coupled to a distal portion of the inner shaft, and a distal end of the second filter is coupled to the first magnet. A second magnet is slidingly coupled to the inner shaft proximal to the first magnet, and a proximal end of the first filter is coupled to the second magnet. A distal end of the first filter is coupled to a proximal end of the second filter. A connector is slidingly coupled to the inner shaft proximal of the second magnet. A plurality of support arms include a proximal end coupled to the connector and a distal end coupled to the filter. The magnets are either magnetically attracted to each other or magnetically repulsed from each other to expand the filter from a radially compressed configuration to a radially expanded configuration. The first filter may be a coarse mesh filter and the second filter may be a fine mesh filter.

BRIEF DESCRIPTION OF DRAWINGS

FIG. 19 is a schematic illustration of an embolic protection device for deployment in a main vessel and in combination with embolic protection devices deployed in branch vessels.

FIG. 19A is a schematic illustration of the embolic protection device of FIG. 19 for deployment in a main vessel.

FIGS. 23 is a schematic illustration of an embolic protection device utilizing magnets for deployment and retrieval thereof, and a method for deploying and retrieving the embolic protection device.

FIG. 24 is a schematic illustration of an embolic protection device utilizing magnets for deployment and retrieval thereof, and a method for deploying and retrieving the embolic protection device.

FIG. 26 is a schematic illustration of an embolic protection device utilizing magnets for deployment thereof, and a method for deploying and retrieving the embolic protection device.

FIG. 27 is a schematic illustration of an embolic protection device utilizing magnets for deployment thereof, and a method for deploying and retrieving the embolic protection device.

FIG. 28 is a schematic illustration of an embolic protection device utilizing magnets for deployment thereof, and a method for deploying and retrieving the embolic protection device.

FIG. 29 is a schematic illustration of an embolic protection device utilizing magnets for deployment thereof, and a method for deploying and retrieving the embolic protection device.

FIG. 30 is a schematic illustration of an embolic protection device utilizing magnets for deployment thereof, and a method for deploying and retrieving the embolic protection device.

FIG. 31 is a schematic illustration of an embolic protection device utilizing magnets for deployment thereof, and a method for deploying and retrieving the embolic protection device.

FIG. 32 is a schematic illustration of an embolic protection device utilizing magnets for deployment thereof and a fluid for retrieval thereof, and a method for deploying and retrieving the embolic protection device.

FIG. 33 is a schematic illustration of an embolic protection device utilizing magnets for deployment thereof and a fluid for retrieval thereof, and a method for deploying and retrieving the embolic protection device.

FIG. 34 is a schematic illustration of an embolic protection device utilizing magnets for deployment thereof and a fluid for retrieval thereof, and a method for deploying and retrieving the embolic protection device.

FIG. 35 is a schematic illustration of an embolic protection device utilizing magnets for deployment thereof, and a method for deploying and retrieving the embolic protection device.

FIG. 36 is a schematic illustration of an embolic protection device utilizing magnets for deployment thereof, and a method for deploying and retrieving the embolic protection device.

FIG. 37 is a schematic illustration of an embolic protection device utilizing magnets for deployment thereof, and a method for deploying and retrieving the embolic protection device.

DETAILED DESCRIPTION

Specific embodiments of the present invention are now described with reference to the figures, wherein like reference numbers indicate identical or functionally similar elements. Unless otherwise indicated, the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. In addition, the term "self-expanding" is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Although the description of the invention is in the embolic filters for use in conjunction with aortic valve procedures, the devices and methods described herein can also be used in conjunction with other procedures at other locations. For example, and not by way of limitation, the devices and methods described herein could be used for percutaneous mitral valve replacements, coronary artery stenting procedures, and carotid artery stenting procedures. Furthermore, there is no intention to be bound by any expressed or implied theory presented in the preceding technical field, background, brief summary or the following detailed description.

Figure 1:
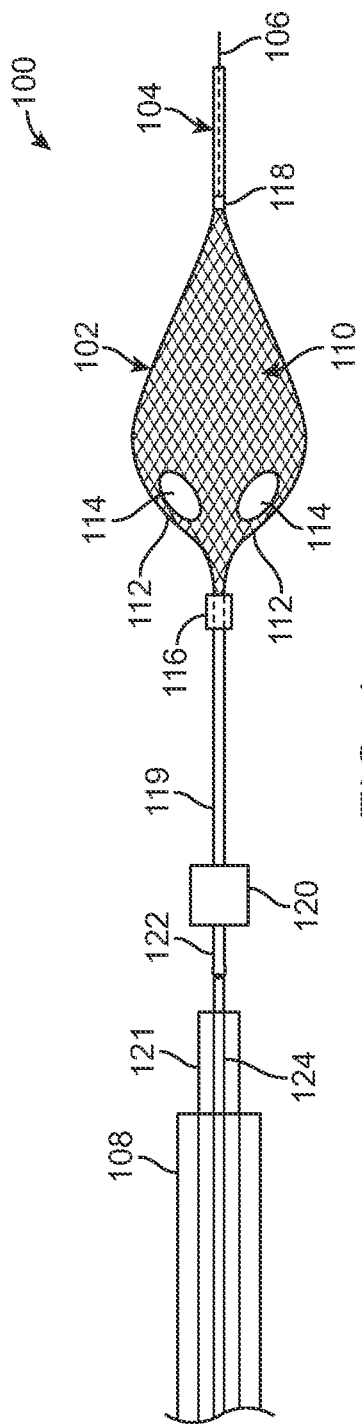
FIG. 1 is a schematic illustration of an embolic protection device with the filter in a deployed or expanded configuration.
Figure 2:
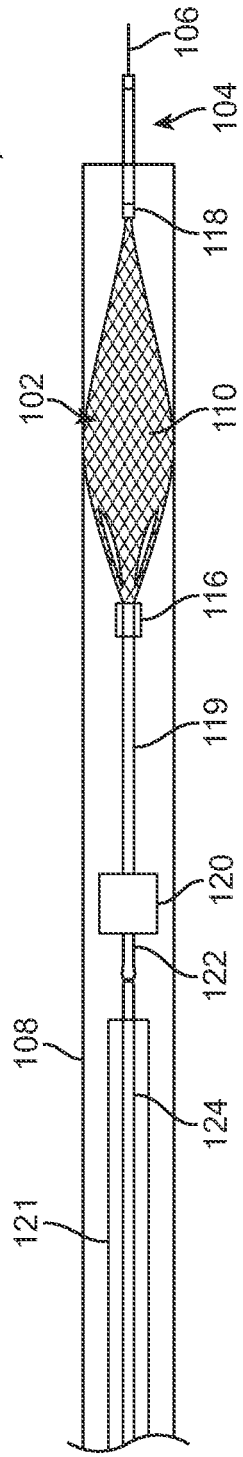
FIG. 2 is a schematic illustration of the embolic protection device of FIG. 1 in the delivery or radially compressed configuration.

Embodiments hereof are directed to embolic protection devices. In particular, embodiments hereof are directed to embolic protection devices including magnets and methods for using such devices. FIG. 1 shows an embodiment of an embolic protection device 100. Embolic protection device 100 includes a filter assembly 102 located adjacent the distal end 104 of a delivery member 106. Delivery member 106 can be a modified guidewire assembly, hereinafter referred to as either "delivery member" or "guidewire". Filter assembly 102 is delivered, deployed and retrieved by a sheath 108 arranged to be slid over filter assembly 102. When embolic protection device 100 is in a constrained position, filter assembly 102 is collapsed within sheath 108 as shown in FIG. 2. When filter assembly 102 is deployed, sheath 108 is withdrawn, releasing filter assembly 102 as shown in FIG. 1.

Filter assembly 102 includes a filter 110 and connecting struts 112 connecting a proximal end of filter 110 to guidewire 106. In particular, as shown in FIG. 1, connecting struts 112 may be the wires or strands that form filter 110 grouped to form the connecting struts 112 and openings 114 between connecting struts 112. Alternatively, connecting struts 112 may be separate from filter 110 and be connected thereto, as described, for example, in U.S. Pat. No. 6,346,116 to Brooks et al., the contents of which are incorporated in their entirety by reference herein. Connecting struts 112 are secured to a tether 119 at a proximal connection 116 and distal end of filter assembly 102 is secured to guidewire 106 at a distal connection 118, as shown in FIG. 1. Tether 119 and guidewire 106 may be extensions of each other or may be separate elements. In an embodiment, connections 116, 118 are fixed in longitudinal positions but are capable of rotational movement independent of the guidewire core while maintaining the longitudinal position.

In the embodiment of FIGS. 1-2, filter 110 is a braided self-expanding or shape memory material, such as Nitinol. Filter 110 is shape set to return to the configuration shown in FIG. 1 upon release from sheath 108. However, other filters and filter materials may be used. For example, and not by way of limitation, filter assembly 102 may be similar to Medtronic's Defender embolic protection filter, with modifications described herein. Further, filter assembly 102 may be similar to the filter assemblies described in U.S. Pat. No. 6,346,116 to Brooks et al., the content of which is incorporated by reference herein. Other filter assemblies known to those skilled in the art may also be utilized.

Figure 1A:
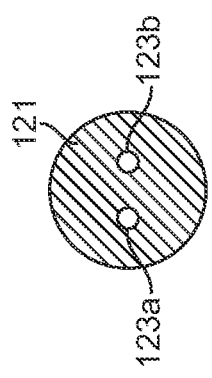
FIG. 1A is a cross-sectional view of a portion of the embolic protection device of FIG. 1.
Figure 9:
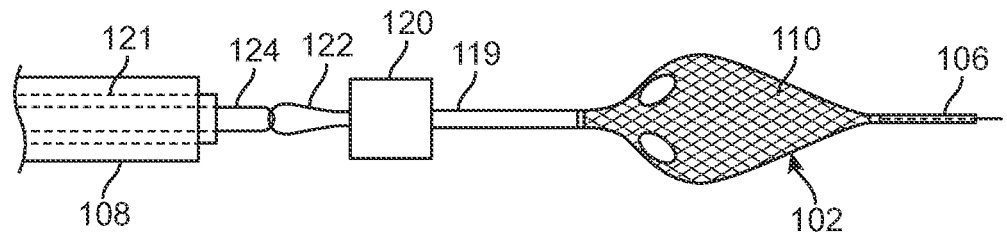
FIG. 9 is a schematic detailed view of a portion of the embolic protection device of FIG. 1.

Embolic protection device 100 further includes a magnet 120 coupled to a proximal end of tether 119. Magnet 120 may be coupled to tether 119 by devices and methods known to those skilled in the art, such as adhesives and mechanical fasteners. Magnet 120 may be a magnetic material or a material capable of being magnetized. Coupled to a proximal portion of magnet 120 is a wire loop 122, which is coupled to a tether 124. Wire loop 122 and tether 124 may be any construction which allows magnet 120 and filter assembly 102 to be disconnected from tether 124 after deployment at a desired location. In the embodiment shown in FIGS. 1-2 (and shown in more detail in FIG. 9), a multi-lumen shaft 121 is disposed within sheath 108. Sheath 108 moves freely in an axial direction over multi-lumen shaft 121. FIG. 1A shows a cross-section of multi-lumen shaft 121, including lumens 123a and 123b. Tether 124 extends the length of the inner shaft 121 from a proximal end thereof through lumen 123a, extends out of a distal end of lumen 123a, loops through wire loop 122, and back proximally through lumen 123b of multi-lumen shaft 121. Ends of tether 124 are anchored to a handle (not shown) during navigation and deployment of embolic protection device 100.

Figure 6:
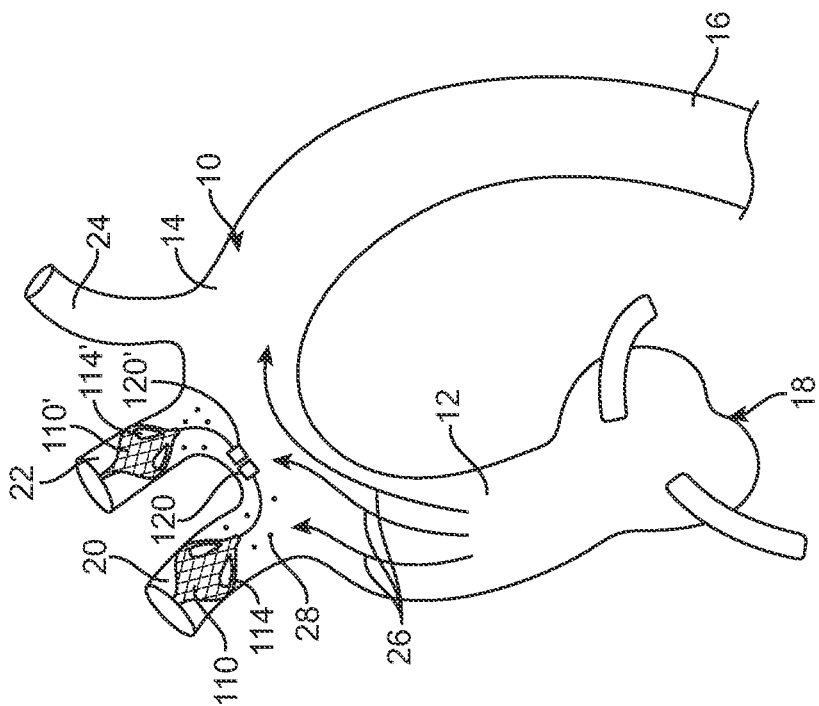
FIG. 6 is a schematic illustration of a step in a method of delivering and deploying two embolic protection devices and coupling them together using magnets, and then retrieving the embolic protection devices after a procedure is completed.

FIGS. 3-8 show a method of delivering and deploying a pair of embolic protection devices 100 in branch vessels of the aortic arch 14, in particular, the brachiocephalic artery 20 (also known as the innominate artery) and the left common carotid artery 22. As shown in FIGS. 3-8, the aorta 10 includes the ascending aorta 12, the aortic arch 14, and the descending aorta 16. Between the ascending aorta 12 and the left ventricle (not shown) of the heart (not shown) is the aortic valve 18. Branching from the aortic arch 14 are the brachiocephalic artery 20, the left common carotid artery 22, and the left subclavian artery 24. The brachiocephalic artery 20 branches into the right subclavian artery (not shown) and the right common carotid artery (not shown). During procedures to repair or replace the aortic valve 18, embolic debris may be dislodged and be delivered downstream with blood flow as shown in FIG. 6. Embolic filters or distal protection devices are utilized to prevent the debris from reaching and blocking narrower vessels. In particular, the right common carotid artery (not shown), which branches from the brachiocephalic artery 20, and the left common carotid artery 22 are particularly sensitive to embolic debris because they lead to the vessels of the brain. Accordingly, FIGS. 3-8 show embolic protection devices 100 delivered and deployed in the brachiocephalic artery 20 and the left common carotid artery 22. However, those of ordinary skill in the art would recognize that the devices and methods described herein may be utilized in other locations.

Figure 4:
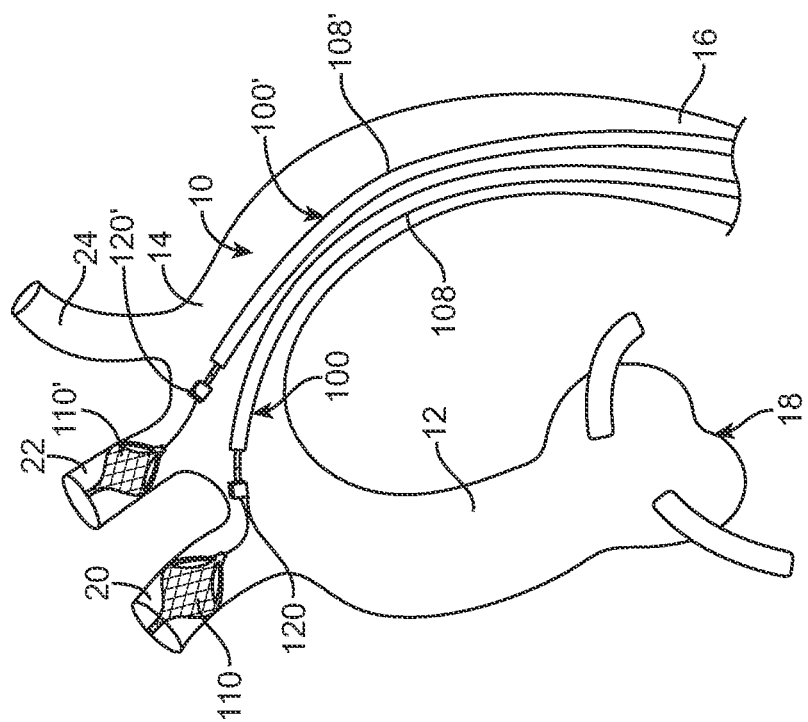
FIG. 4 is a schematic illustration of a step in a method of delivering and deploying two embolic protection devices and coupling them together using magnets, and then retrieving the embolic protection devices after a procedure is completed.
Figure 3:
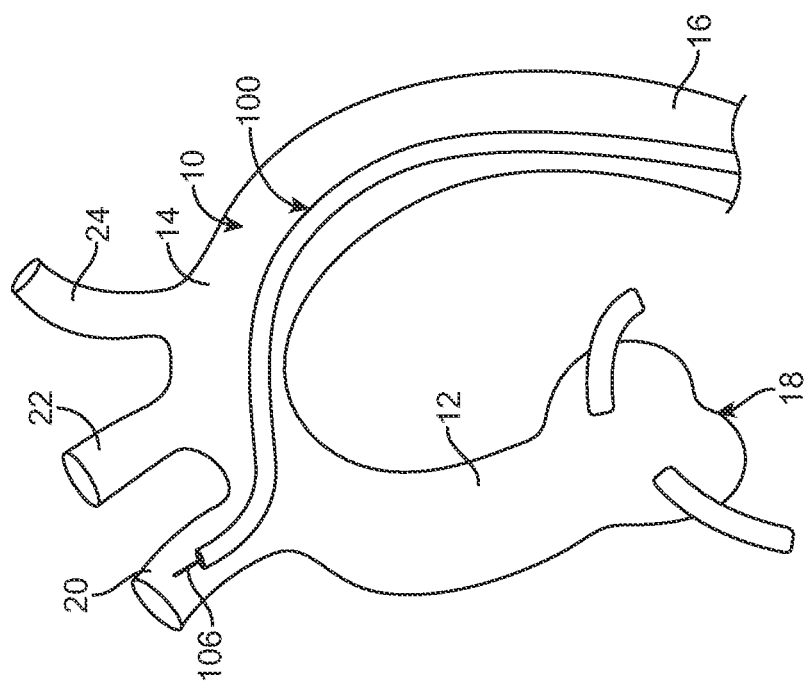
FIG. 3 is a schematic illustration of a step in a method of delivering and deploying two embolic protection devices and coupling them together using magnets, and then retrieving the embolic protection devices after a procedure is completed.

As shown in FIG. 3, a first embolic protection device 100 is advanced from the descending aorta 16 into the aortic arch 14 and into brachiocephalic artery 20. Embolic protection device 100 may be advanced by access through the femoral artery using, for example, the Seldinger technique. Other methods known to those skilled in the art may also be utilized. A second embolic protection device 100' is also advanced through the descending aorta 16 into the aortic arch 14, and into the left common carotid artery 22, as shown in FIG. 4. The second embolic protection device 100' may also be advanced by access through the femoral artery. However, the access for one of the embolic protection devices may be through the left femoral artery to the left common iliac artery and into the descending aorta 16, while access for the other of the embolic protection devices may be through the right femoral artery to the right common iliac artery and into the descending aorta. Other access sites and paths may be utilized, as known to those skilled in the art.

After embolic protection devices 100, 100' have reached into the brachiocephalic artery 20 and the left common carotid artery 22, respectively, sheaths 108, 108' are retracted such that filters 110, 110' are expanded within the respective artery, as shown in FIG. 4. The order of deployment of the baskets is not critical. For example, and not by way of limitation, second embolic protection device 100' may be delivered first, and sheath 108' may be retracted to deploy filter 110'. Then first embolic protection device 100 may be delivered and sheath 100 may be retracted to deploy filter 110, or the order may be reversed. Also, one of the two embolic protection devices may be delivered, then the other may be delivered, and then the filters can be deployed.

Figure 5:
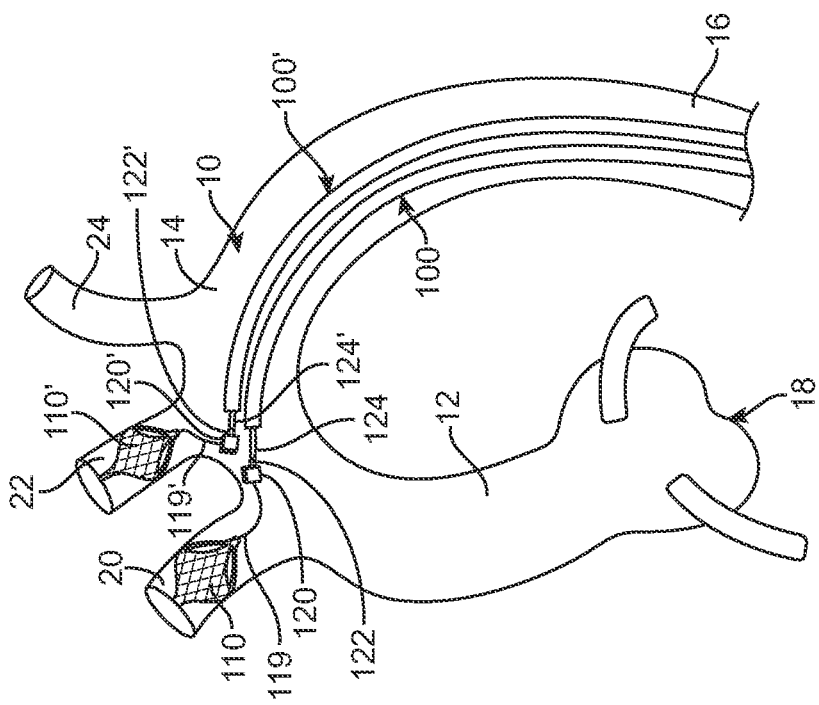
FIG. 5 is a schematic illustration of a step in a method of delivering and deploying two embolic protection devices and coupling them together using magnets, and then retrieving the embolic protection devices after a procedure is completed.

With the filters 110, 110' deployed within their respective arteries, and the magnets 120, 120' exposed by retraction of sheaths 108, 108', the embolic protections devices 100, 100' are maneuvered such that magnets 120, 120' are sufficiently close to each other magnetically couple to the each other, as shown in FIG. 5. Once magnets 120, 120' are coupled to each other, wire loops 122, 122' are disconnected from tethers 124, 124', respectively. Tethers 124, 124' are disconnected from wire loops 122, 122' by unlocking the proximal ends of the respective tether 124, and pulling on one of the ends until the entire tether 124 is removed. Alternatively, tethers 124, 124' may be a suture material formed into a loop that is cut to release wire loops 122, 122', or a mechanical loop that in unhinged or mechanically opened to release wire loops 122, 122', or any other releasable connection known to those skilled in the art. Sheaths 108, 108' with tethers 124, 124' may be retracted out of the body, leaving filter assembly 102/filter 110 deployed within the brachiocephalic artery 20, and filter assembly 102'/filter 110' deployed within left common carotid artery 22, as shown in FIG. 6. Further, the filter assemblies 102, 102' are coupled together via tethers 119, 119' extending into the aortic arch 14 and being coupled together via magnets 120, 120', as also shown in FIG. 6. With the filters deployed as shown in FIG. 6, procedures for the aortic valve, such as TAVI or valvuloplasty, may access the aortic valve area through the aortic arch 14 with minimal interference from the embolic protections devices. During the procedure, embolic debris 28 travelling along the blood flow represented by arrows 26 will be captured by filters 110, 110'.

Figure 7:
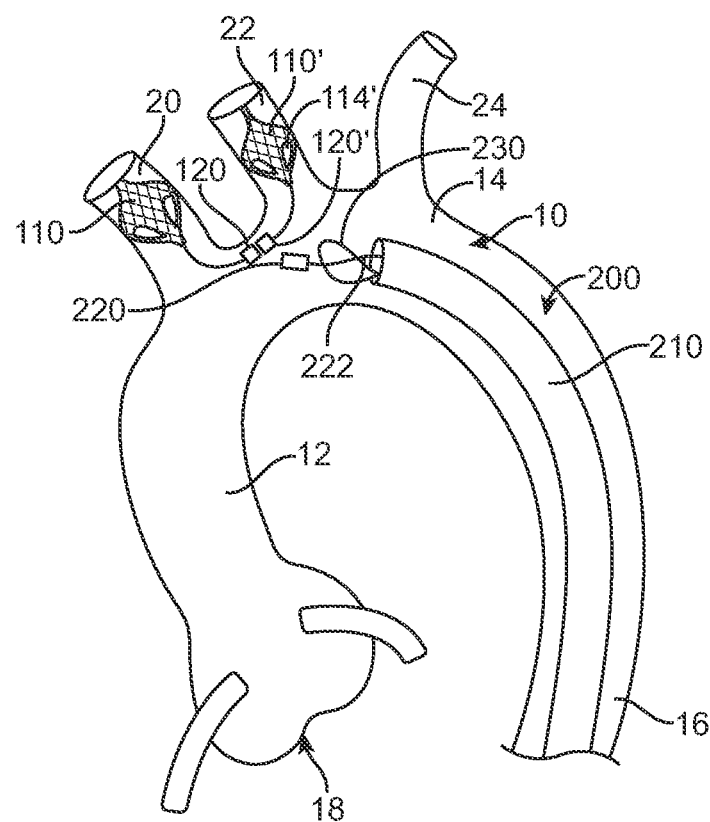
FIG. 7 is a schematic illustration of a step in a method of delivering and deploying two embolic protection devices and coupling them together using magnets, and then retrieving the embolic protection devices after a procedure is completed.
Figure 7A:
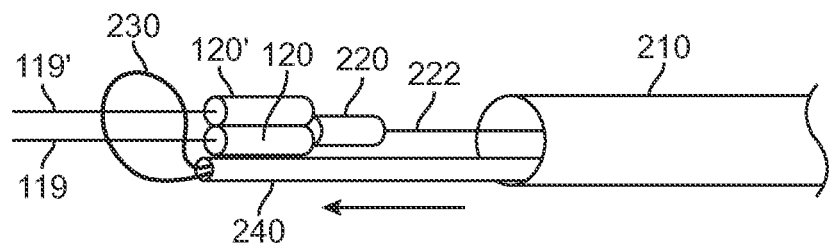
FIG. 7A is a schematic detail of a step of the method illustrated in FIGS. 7-8.
Figure 7B:
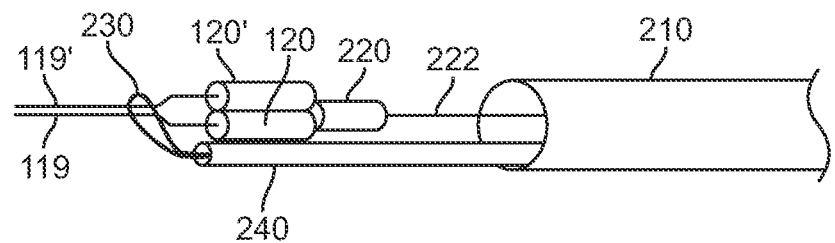
FIG. 7B is a schematic detail of a step of the method illustrated in FIGS. 7-8.
Figure 7C:
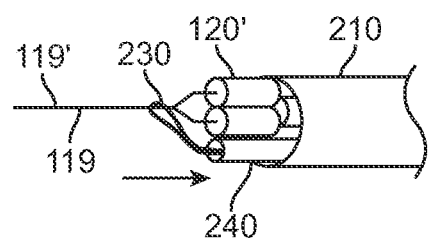
FIG. 7C is a schematic detail of a step of the method illustrated in FIGS. 7-8.
Figure 8:
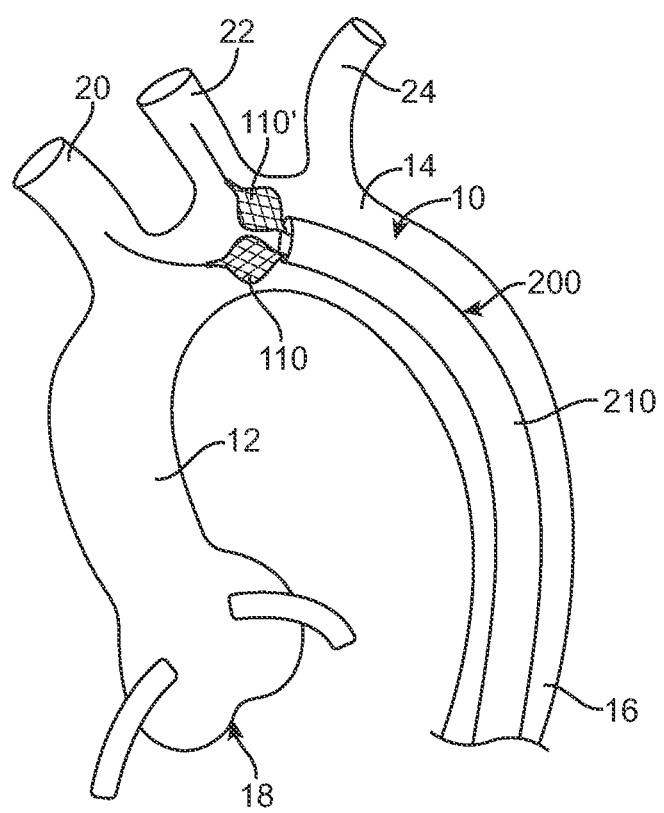
FIG. 8 is a schematic illustration of a step in a method of delivering and deploying two embolic protection devices and coupling them together using magnets, and then retrieving the embolic protection devices after a procedure is completed.

After the procedure is completed and the procedure devices have been removed, the filters 110, 110' may be removed. In order to remove the filters, a retrieval catheter 200 is advanced adjacent the location of the magnets 120, 120'. Retrieval catheter 200 includes a catheter shaft 210 and a retrieval magnet 220 disposed at a distal end of a shaft or wire 222. Retrieval catheter 200 also includes a snare 230 coupled to shaft 222. With retrieval catheter 200 adjacent magnets 120, 120', retrieval magnet 220 is extended from catheter shaft 210 by distally extending shaft 222 or retracting catheter shaft 210, as shown in FIG. 7. Retrieval magnet 220 is magnetically coupled to magnets 120, 120'. Snare 230 is then extended over magnets 120, 120', 220 and tightened. Snare 230 is a pre-shaped loop formed using nitinol or other shape memory material to have an opening large enough to easily clear the magnets 120, 120', 220. Similar to tether 124 described above, snare 230 is a wire with a first end disposed at a proximal end (not shown) of a tube 240. The wire extends distally within tube 240 and out of a distal end of tube 240, forming a loop and extending back proximally to a second end also disposed at a proximal end of tube 240. Tube 240 is advanced from the distal end of the catheter shaft 210 such that snare 230 extends distally beyond the magnets 120, 120', 220, as shown in FIG. 7A. Pulling both ends of the proximal end of the wire forming snare 230 closes snare 230 around tethers 119, 119' as shown in FIG. 7B. Shaft 222 and tube 240 are then simultaneously retracted proximally, pulling magnets 120, 120', 220 and filters 110, 110' into catheter shaft 210, as shown in FIGS. 7C and 8. Catheter shaft 210, with filters 110, 110' disposed therein, may then be removed from the body. Alternatively, once filters 110, 110' removed from the branch vessels, shaft 210 may be advanced distally over filters 110, 110' and then catheter 210 with filters 110, 110' disposed therein may be removed from the body.

Embolic protection device 100 as described above and used in the method described in FIGS. 3-8 may be modified for various reasons. For example, and not by way of limitation, different filters and delivery devices may be used. In another non-limiting example, it may be desirable to ensure that the magnetic connection between magnets 120, 120' is properly made a sufficiently secure to prevent filters 110, 100' from moving downstream.

Figure 10:
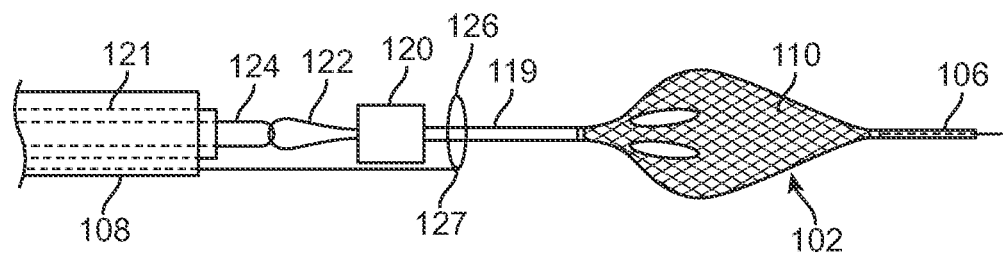
FIG. 10 is a schematic detailed view of a portion of the embolic protection device of FIG. 1 with the addition of a snare.

FIG. 10 shows an embodiment of a modification to embolic protection device 100 to ensure that magnets 120, 120' are properly coupled before releasing wire loop 122 from tether 124. In particular, a releasable snare 126 extends from sheath 108 distally past magnet 120 and around tether 119. Snare 126 is in this position during delivery of embolic protection device 100 and retraction of sheath 108 to deploy filter assembly 102. After magnets 120, 120' have been magnetically coupled together, wire loop 122 is released from tether 124, as described above. However, if the magnetic attraction between magnets 120, 120' is not sufficient, or for some other reason the magnets 120, 120' become detached, snare 126 catches magnet 120, preventing release of filter assembly 102 from sheath 108. Snare 126 can be retracted to recapture magnet 120 and filter assembly 102 into sheath 108. If the magnetic connection between magnets 120, 120' is sufficient, snare 126 is released and the procedure proceeds as described above. Snare 126 may be similar to snare 230 described above with respect to FIGS. 7A-7C or tether 124 described above. In such an embodiment, if the magnetic attraction between magnets 120, 120' is sufficient, one end of the wire forming snare 126 is pulled proximally until the second end extends distally and then back proximally to withdraw the wire from the body. Alternatively, snare 126 may include a slip-knot 127 as shown in FIG. 10. In such an embodiment, if the magnetic connection between magnets 120, 120' is sufficient, proximal end of the wire of snare 126 is pushed to enlarge the size of the loop of snare 126. The wire is then pulled such that snare 126 extends proximally over magnet 120 and is removed from the body through sheath 108. Each embolic protection device 100, 100' can have this feature, or only one of the two can have it. If only one includes this feature, its wire loop 122 and tether 124 should be released first.

Figure 11:
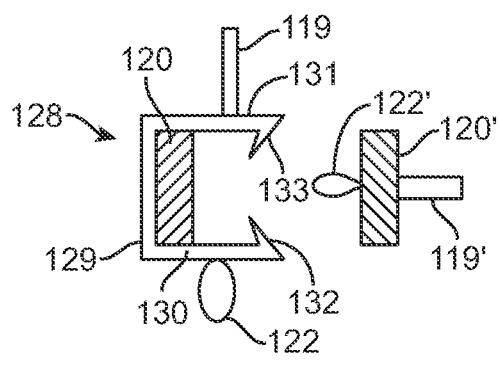
FIG. 11 is a schematic illustration of a locking mechanism coupled to a magnet of an embolic protection device.
Figure 12:
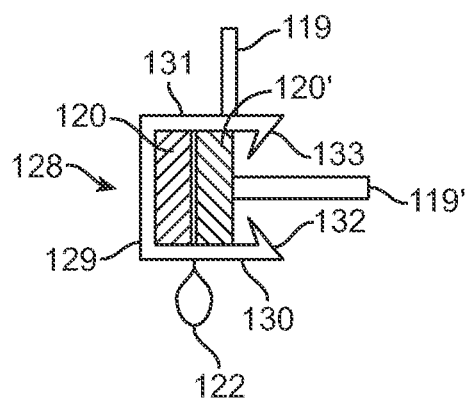
FIG. 12 is a schematic illustration of the locking mechanism of FIG. 11 with the magnets of each embolic protection device secured within the locking mechanism.

Other devices may also be used to ensure a strong connection between magnets 120, 120'. For example, the magnetic connection can be supplanted with a mechanical connection. For example, and not by way of limitation, FIGS. 11 and 12 show a modification to magnet 120 to help ensure a secure connection to magnet 120'. In particular, a locking mechanism 128 is coupled to magnet 120. Locking mechanism 128 includes a first wall 129 with second and third walls 130, 131 extending substantially perpendicular to first wall 129 and parallel to each other to form three sides of a rectangle. Magnet 120 is coupled to an inside surface of first wall 129. Extending from an end of second wall 130 opposite first wall 129 is a latch 132. Latch 132 extends toward the interior of the three-sided rectangle formed by first, second, and third walls 129, 130, 131. In the embodiment shown, latch 132 also extends towards first wall 129. Similarly, extending from an end of third wall 131 opposite first wall 129 is a latch 133. Latch 133 extends toward the interior of the three-sided rectangle formed by first, second, and third walls 129, 130, 131. In the embodiment shown, latch 133 also extends towards first wall 129. Wire loop 122, described above, is coupled to an outside surface of second wall 130 and tether 119 is coupled to an outside surface of third wall 131, as shown in FIG. 11. Accordingly, filter assembly 102 (not shown in FIGS. 11-12) is coupled tether 119 opposite locking mechanism 128. When locking assembly 128 with magnet 120 disposed therein is located adjacent to magnet 120', magnets 120 and 120' are attracted to each other such that magnet 120 enters into the three-sided rectangle formed by walls 129, 130, 132 from the open-end thereof, as shown in FIG. 12. Latches 132, 133 prevent magnet 120' from exiting the three-sided rectangle, thereby preventing detachment of magnets 120, 120'. In FIG. 12, wire loop 122' is not shown, but is disposed between magnets 120, 120'.

Figure 39:
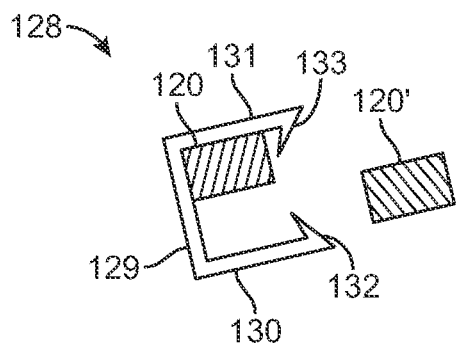
FIG. 39 is a schematic illustration of the locking mechanism of FIGS. 11-12 with the magnets of the embolic protection devices in an alternative configuration.
Figure 40:
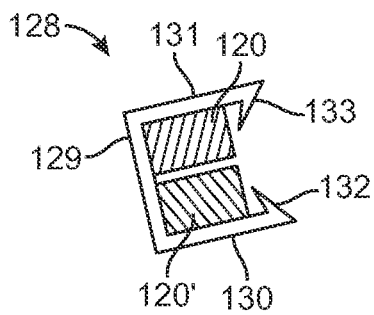
FIG. 40 is a schematic illustration of the locking mechanism of FIGS. 11-12 with the magnets of the embolic protection devices in an alternative configuration.
Figure 41:
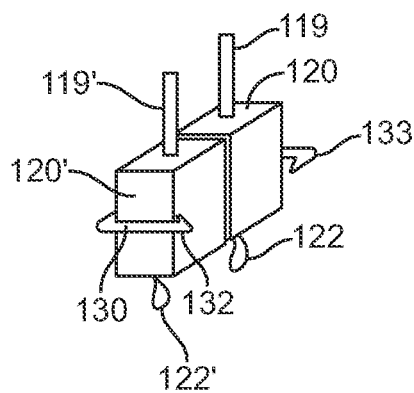
FIG. 41 is a schematic illustration of the locking mechanism of FIGS. 11-12 with the magnets of the embolic protection devices in an alternative configuration.

FIGS. 39-41 show locking mechanism 128 in another configuration. In particular, in the embodiment of FIGS. 39-41, magnets 120, 120' are disposed side-by-side in locking mechanism 128, instead of one in front of the other. As can be seen in FIGS. 40 and 41, when magnets 120, 120' are disposed within locking mechanism 128, both magnets abut against first wall 129. Magnet 120 also abuts against third wall 131 and magnet 120' also abuts against second wall 130. As shown in FIG. 39, magnet 120 is disposed within locking mechanism 128 when embolic protection device 100 is delivered to the implantation site. Magnet 120 may be attached to locking mechanism any manner know to those skilled in the art, such as by an adhesive of mechanical connection. Also, because magnet 120 is attached to locking mechanism 128, latch 133 may be excluded in this embodiment. Magnet 120' is attracted to magnet 120 such that adjacent sides are attracted to each other, as shown in FIGS. 40 and 41.

Figure 13:
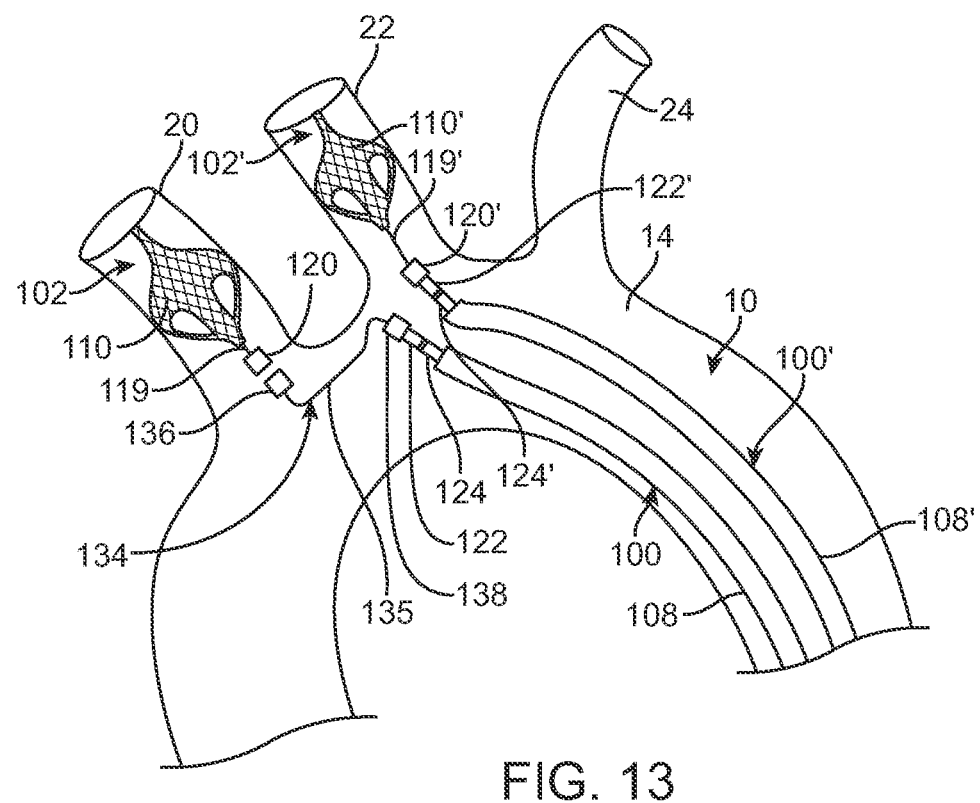
FIG. 13 is a schematic illustration of an embodiment of embolic protection devices with shorter tethers and a coupling tether, and a method of coupling the embolic protection devices together using the coupling tether.
Figure 14:
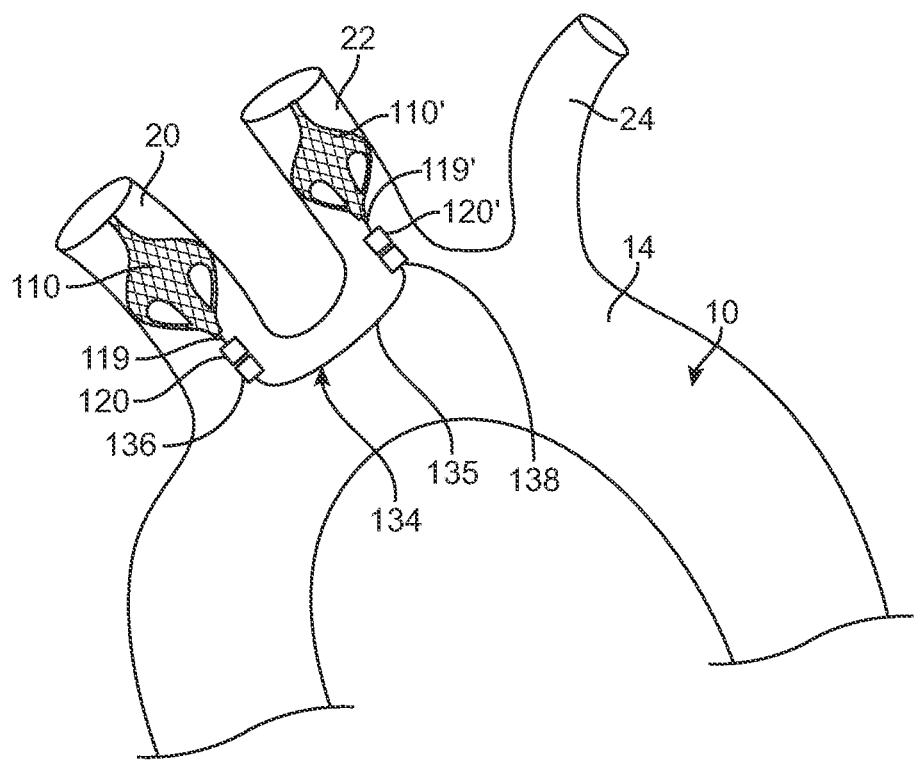
FIG. 14 is a schematic illustration of an embodiment of embolic protection devices with shorter tethers and a coupling tether, and a method of coupling the embolic protection devices together using the coupling tether.
Figure 16:
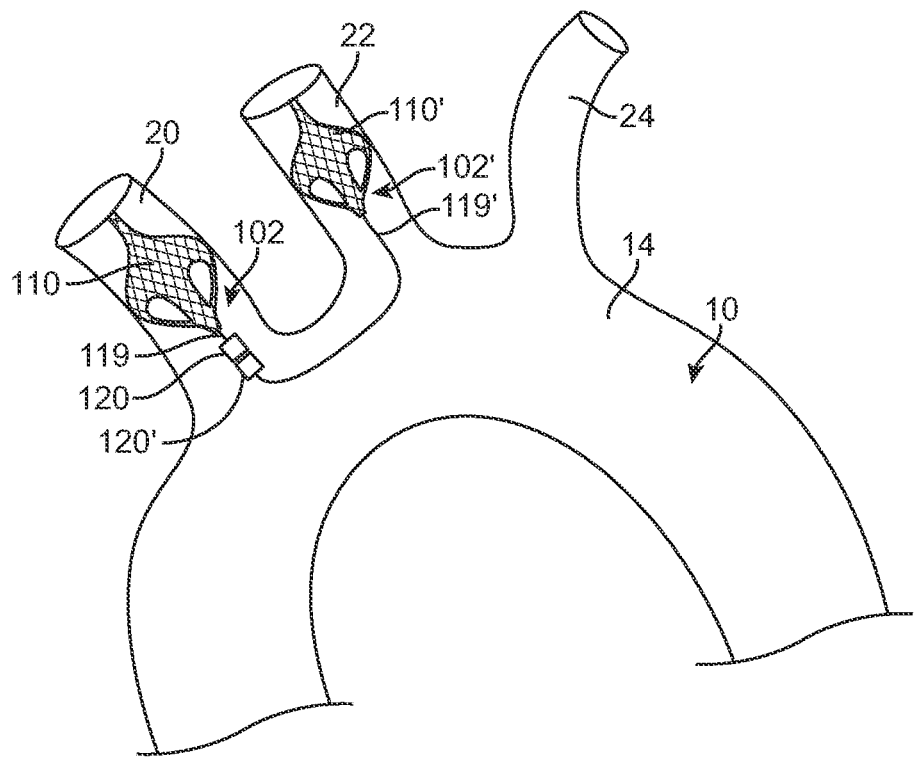
FIG. 16 is a schematic illustration of embolic protection devices wherein one of the embolic protection devices includes a short tether and the other includes a long tether, and of a step in a method of deploying and retrieving the embolic protection devices.

FIGS. 13-14 show an embodiment of embolic protection devices 100, 100' with modifications to keep magnets 120, 120' out of the aortic arch 14 so that magnets 120, 120' do not interfere with devices extending through the aorta 10, such as devices for a TAVI procedure. In particular, tethers 119, 119' of embolic protection devices 100, 100' are of a length such that magnets 120, 120' do not extend into the aorta 10. In order to couple the filters 110, 110' to each other to prevent downstream migration, a connecting device 134 couples magnet 120 of embolic protection device 100 to magnet 120' of embolic protection device 100'. In particular, as shown in FIG. 13, embolic protection device 100 includes filter assembly 102, tether 119, and magnet 120. Additionally, a first magnet 136 of connecting device 134 is coupled to magnet 120. A connecting wire 135 is coupled to first magnet 136 at a first end of wire 135. Disposed at a second end of connecting wire 135 is a second magnet 138. Second magnet 138 is coupled to wire loop 122 and tether 124, as described above with respect to FIGS. 1 and 9. Embolic protection device 100' is as described above with respect to FIGS. 1 and 9, except that tether 119 is of a length that it does not extend to aorta 10 when filter assembly 102 is deployed within left common carotid artery 22. With sheaths 108, 108' retracted to deploy filters 110, 110', respectively, sheaths 108, 108' are manipulated such that second magnet 138 is disposed adjacent magnet 120', as shown in FIG. 13. When a magnetic connection is established between second magnet 138 and magnet 120' of embolic protection device 100', wire loop 122 attached to second magnet 138 may be disconnected from tether 124 and wire loop 122' attached to magnet 120' may be disconnected from tether 124', as described above. Sheath 108, 108' are removed from the aorta, leaving filter assemblies 102, 102' and connecting device 134, as shown in FIG. 14. With the filters deployed as shown in FIG. 16, procedures for the aortic valve, such as TAVI or valvuloplasty, may access the aortic valve area through the aortic arch 14 with minimal interference from the embolic protection devices. After the completion of the procedures, filter assemblies 102, 102' may be recaptured as explained above with respect to FIGS. 7-8.

Figure 15:
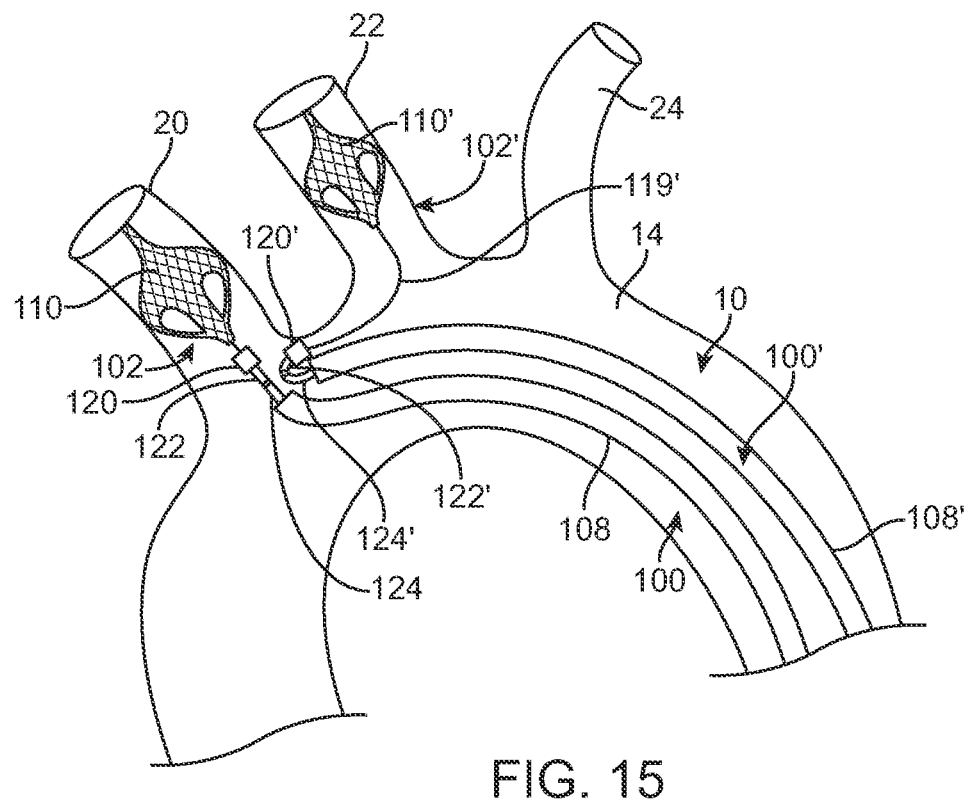
FIG. 15 is a schematic illustration of embolic protection devices wherein one of the embolic protection devices includes a short tether and the other includes a long tether, and of a step in a method of deploying and retrieving the embolic protection devices.
Figure 17:
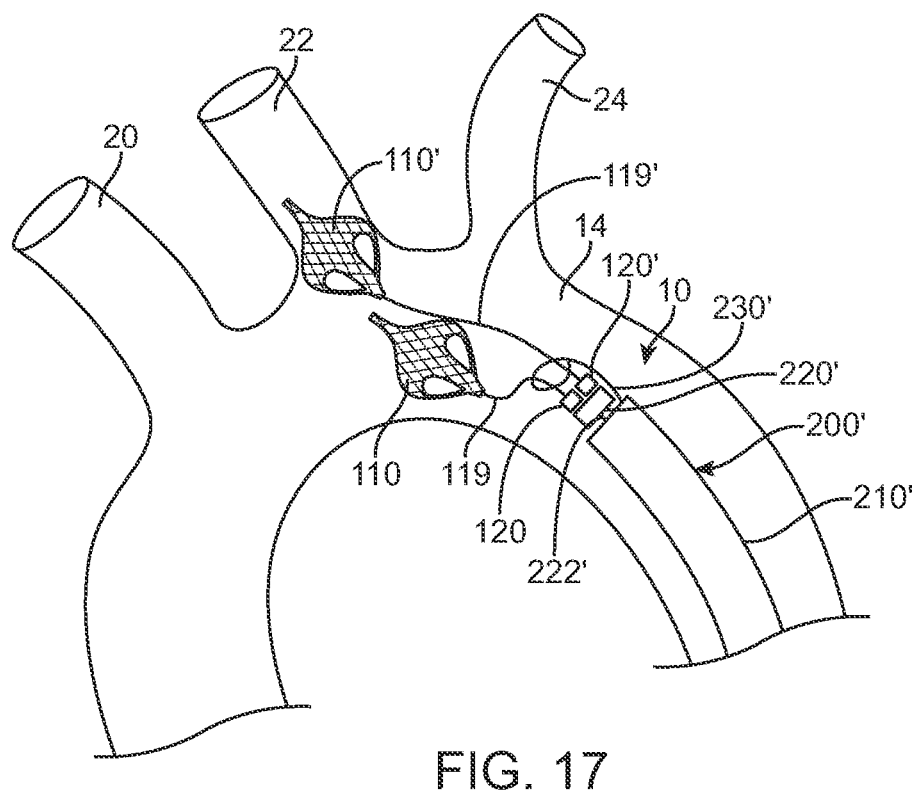
FIG. 17 is a schematic illustration of embolic protection devices wherein one of the embolic protection devices includes a short tether and the other includes a long tether, and of a step in a method of deploying and retrieving the embolic protection devices.

FIGS. 15-17 show schematically an embodiment of embolic protection devices 100, 100'. Embolic protection devices 100, 100' are similar to embolic protection device 100 described above with respect to FIGS. 1-9. However, tether 119 of embolic protection device 100 is relatively shorter than described above such that magnet 120 does not extend into aorta 10. Further, tether 119' of embolic protection device 100' is relatively longer such that tether 119' extends from left common carotid artery 22, into aortic arch 14, and into brachiocephalic artery 20, as shown in FIG. 16. Accordingly, after sheaths 108, 108' have been retracted to deploy filters 110, 110' and expose magnets 120, 120', as described above with respect to FIGS. 3-4, the embolic protection devices 100, 100' are maneuvered such that magnets 120, 120' are sufficiently close to each other magnetically couple to the each other, as shown in FIG. 15. Once magnets 120, 120' are coupled to each other, wire loops 122, 122' are disconnected from tethers 124, 124', respectively, as described above. Sheaths 108, 108' with tethers 124, 124' may be retracted out of the body, leaving filter assembly 102/filter 110 deployed within the brachiocephalic artery 20, and filter assembly 102'/filter 110' deployed within left common carotid artery 22, as shown in FIG. 16. Further, the filter assemblies 102, 102' are coupled together via tethers 119, 119', but only tether 119' extends into aorta 10, and magnets 120, 120' are both disposed in the brachiocephalic artery 20, as also shown in FIG. 16. With the filters deployed as shown in FIG. 16, procedures for the aortic valve, such as TAVI or valvuloplasty, may access the aortic valve area through the aortic arch 14 with minimal interference from the embolic protection devices. It would be understood by those skilled in the art that although FIGS. 15 and 16 show a short tether 119 associated with the filter 110 deployed in the brachiocephalic artery 20 and a long tether 119' associated with the filter 110' deployed in the left common carotid artery, the locations can be reversed such that the long tether extends from the brachiocephalic artery 20, into the aortic arch 14, and into the left common carotid artery 22, where the magnets 120, 120' are coupled to each other.

After the procedure is completed and the procedure devices have been removed, the filters 110, 110' may be removed. In order to remove the filters, a retrieval catheter 200' is advanced adjacent the location of the magnets 120, 120', as described above with respect to FIG. 7. Retrieval catheter 200' includes a catheter shaft 210' and a retrieval magnet 220' disposed at a distal end of a shaft or wire 222'. Retrieval catheter 200' also includes a snare 230' coupled to shaft 222'. With retrieval catheter 200' maneuvered such that it is adjacent magnets 120, 120', retrieval magnet 220' is extended from catheter shaft 210' by distally extending shaft 222' or retracting catheter shaft 210', as described above with respect to FIG. 7. However, due to the location of magnets 120, 120', this recapture will take place within one of the brachiocephalic artery 20 or left common carotid artery 22, depending on where the magnets 120, 120' are coupled to each other. Retrieval magnet 220' is magnetically coupled to magnets 120, 120'. Snare 230' is then extended over magnets 120, 120', 220 and tightened, as described above with respect to FIGS. 7A-7C. Shaft 222' is then retracted proximally, pulling magnets 120, 120', 220' and filters 110, 110' into catheter shaft 210', as shown in FIG. 17. Catheter shaft 210', with filters 120, 120' disposed therein, may then be removed from the body. Further, as shown in FIG. 17, because tether 119' is longer than tether 119, when the filters 110, 110' are retracted into catheter shaft 210', the filters 110, 110' enter catheter shaft 210' sequentially or serially, rather than simultaneously or in parallel as shown in FIGS. 7-8. Accordingly, catheter shaft 210' utilized with the embodiment of FIGS. 15-17 may be smaller in diameter than catheter shaft 210 described above with respect to FIGS. 7-8. Further, although FIGS. 15 and 16 show the magnets 120, 120' both disposed in a single branch artery, it would be understood by those skilled in the art that the tethers 119, 119' can be of different lengths with the magnets 120, 120' both disposed in the aorta (main vessel). In such an embodiment the different length tethers 119, 119' provide the benefit that filters 110, 110' enter catheter shaft 210' sequentially or serially, rather than simultaneously or in parallel, as described above.

Figure 18:
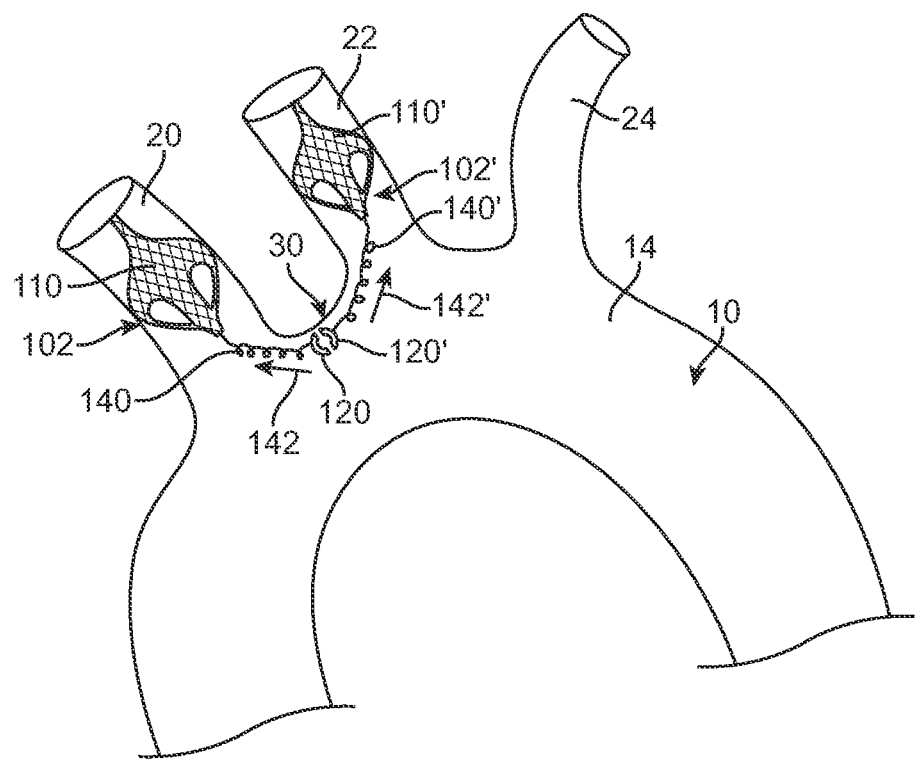
FIG. 18 is a schematic illustration of embolic protection devices with spring-like tethers and C-shaped magnets, and a method of deploying such embolic protection devices.

In another embodiment shown in FIG. 18, tethers 119, 119' of embolic protection devices 100, 100' are replaced with spring tethers 140, 140'. Spring tethers 140, 140' may be any material or shape such that each tether 140, 140' tends to gather or shorten toward its respective filter 110, 110'. In other words tethers 140, 140' provide a force in the direction of arrows 142, 142'. This shortening force may be provided by making tether 140, 140' out of a shape memory material that tends to return to its original coiled shape, or by creating a spring force by the shape of the tether 140, 140', such as a commonly known spring shape. The magnetic attraction between magnets 120, 120' is greater than the shortening forces 142, 142' such that magnets 120, 120' remain coupled to each other. However, the shortening forces 142, 142' take up any slack in tethers 140, 140' such that tethers 140, 140' do not hang or extend into the middle of aorta 10, thereby possibly interfering with procedure devices extending through the aorta 10. Thus, tethers 140, 140' and magnets 120, 120' are pulled against the aortic wall 30 between the brachiocephalic artery 20 and the left common carotid artery 22, as shown in FIG. 18. FIG. 18 also shows the magnets 120, 120' may be C-shaped. However, as would be understood by those skilled in the art, magnets 120, 120' of this embodiment or any of the embodiments described herein, may be any shape suitable for coupling filter assemblies 102, 102' to each other.

Figure 38:
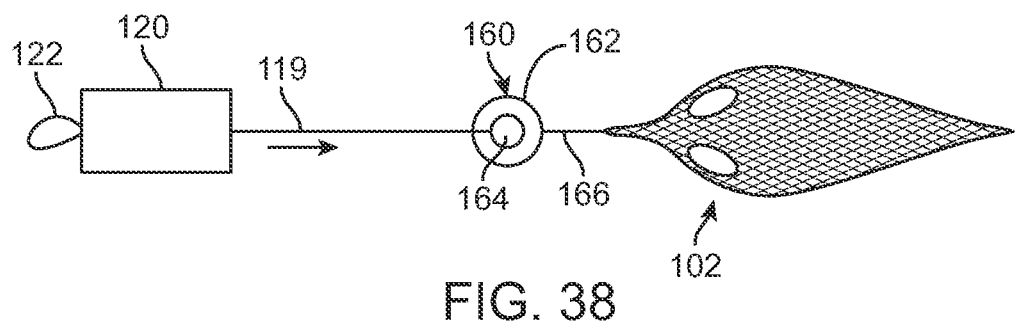
FIG. 38 is a schematic illustration of an embodiment of an embolic protection device with an extendable and retractable tether.

In the embodiments described above with respect to FIGS. 1-18, the tethers described may be retractable and extendable tethers. Accordingly, instead of a long tether and a short tether as described with respect to FIGS. 15-17, one or both of the tethers 119, 119' may be extendable and retractable. FIG. 38 shows tether 119 including a reel 160. Reel 160 includes a housing 162 with a spring 164 disposed within the housing 162. Tether 119 is wrapped around spring 164. A secondary tether 166 couples reel 160 to filter assembly 102. Spring 164 retracts tether 119 in the direction of spring 164, as shown by the arrow in FIG. 38. The retraction force of spring 164 is not sufficient to overcome the attractive magnetic force between magnets 120, 120'. Accordingly, the length of the extendable and retractable tether can be extended such that the magnets can be disposed in the same artery, and the tether can be retracted to take up any slack in the tether such that tethers do not hang or extend into the middle of the aorta 10, as described above with respect to FIG. 18.

FIG. 19 is a schematic illustration of an embolic protection device 300 used in conjunction with embolic protection devices 100, 100' described above. As shown in FIG. 19, embolic protection devices 100, 100' are deployed in the brachiocephalic artery 20 and the left common carotid artery 22, respectively, as described above. Accordingly, magnets 120, 120' connecting filters 110, 110' to each other are disposed within aorta 10 in the region of the aortic arch 14. An additional embolic protection device 300 is deployed in the aorta 10 and magnetically coupled to magnets 120, 120', as shown in FIG. 19. As shown in FIG. 19A, an embodiment of embolic protection device 300 includes a filter 302 and a magnet 304 coupled to filter 302. Filter 302 includes a distal end 306 and a proximal end 308. Proximal end 308 of filter 302 is attached to an outer shaft 312 at a connection 310 such that proximal end 308 does not move relative to outer shaft 312. An inner shaft 314 is disposed through outer shaft 312 and is slidable relative thereto. Distal end 306 of filter 302 is coupled to inner shaft 314, such as by connecting struts 316. Sliding inner shaft 314 relative to outer shaft 312 opens and closes filter 302. Further, inner shaft 302 is sized to permit a procedural catheter 320, such as for a TAVI procedure, to be delivered through a lumen thereof, as shown in FIG. 19. Although a particular embodiment of embolic protection device 300 has been described, those skilled in the art would recognize that any filter device that permits procedural catheter 320 to pass therethrough could be used. For example, and not by way of limitation, filter 302 may be incorporated as part of procedural catheter 320. In one non-limiting example, filter 302 may be a self expanding filter, inner shaft 314 may be eliminated, and distal end 306 of filter 302 may be slidably coupled to procedural catheter 320. Further, the location of magnet 304 on filter 302 may be altered such that the location of filter 302 may be altered. For example, and not by way of limitation, magnet 304 may be disposed at the distal end of filter 302 such that the filter 302 is disposed further downstream in the aorta 10. The location of magnets 120, 120' may also be altered to change the location of filter 302. Other modifications may be made, as known to those skilled in the art.

As shown in FIG. 19, after embolic protection devices 100, 100' have been deployed, embolic protection device 300 is advanced into the aortic arch 14 and deployed such that magnet 304 of filter 302 is magnetically coupled to magnets 120, 120'. Although one magnet 304 is shown, multiple magnets 304 may be distributed around the circumference of filter 302 such that a particular orientation of filter 302 is not required. Upon completion of the procedure filters 110, 110' may be retracted with filter 302 due to the magnetic connection between magnets 120, 120' and magnet 304.

Figure 20:
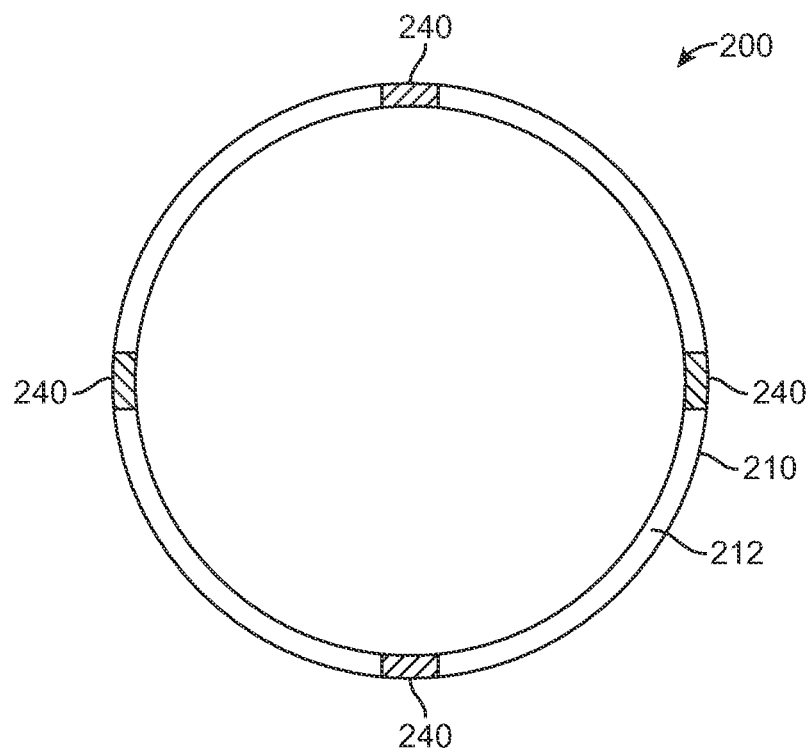
FIG. 20 is a schematic illustration of an embolic protection device and a retrieval catheter with corresponding magnets to magnetically couple the embolic protection device to the retrieval catheter during retrieval of the embolic protection device.
Figure 21:
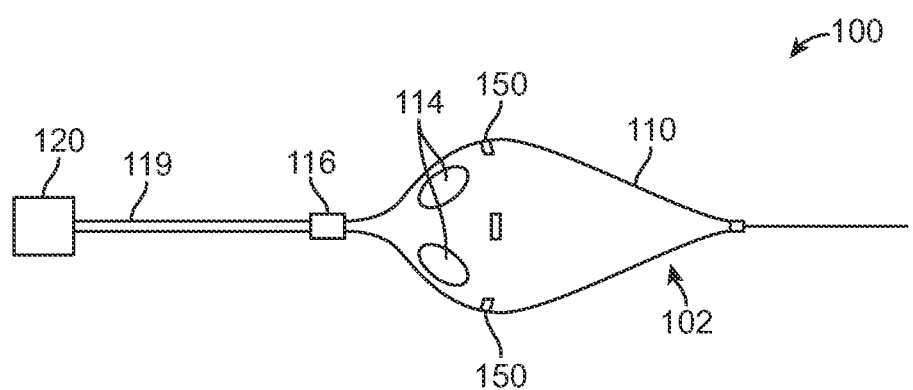
FIG. 21 is schematic illustration of an embolic protection device and a retrieval catheter with corresponding magnets to magnetically couple the embolic protection device to the retrieval catheter during retrieval of the embolic protection device.
Figure 22:
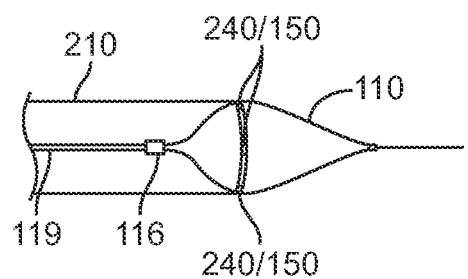
FIG. 22 is schematic illustration of an embolic protection device and a retrieval catheter with corresponding magnets to magnetically couple the embolic protection device to the retrieval catheter during retrieval of the embolic protection device.

FIGS. 20-21 show schematically modifications to embolic protection device 100 and retrieval catheter 200. In particular, embolic protection device 100 as shown in FIG. 21 includes a plurality of magnets 150 coupled to filter 110. Magnets 150 may preferably be located distally of openings 114 and/or at the largest diameter of filter 110. Magnets 150 are disposed around the circumference of filter 110. In one embodiment, four magnets are used, although more or less may be used. Similarly, a distal end 212 of catheter shaft 210 of retrieval catheter 200 includes a plurality of magnets 240 disposed around the periphery thereof. In one embodiment, four magnets 240 are disposed at distal end 212 of catheter shaft 210. However, those skilled in the art would understand that more or less magnets 240 can be used. Further, in an embodiment, the entire distally facing surface of catheter shaft 210 may be a magnet or may be magnetized. Accordingly, when embolic protection device 100 is retracted towards catheter shaft 210, as described above with respect to FIGS. 7-8, magnets 150 on filter 110 and magnets 240 on distal end 212 of catheter shaft 210 are attracted to each other, magnetically coupling catheter shaft 210 and filter 110, as shown in FIG. 22. Catheter shaft 210 can then be removed from the body, with filter 110 coupled to distal end 212 thereof. In some instances with certain filters, embolic debris may be released from filters when the filters are collapsed for removal from the body. By not collapsing filter 110 for removal from the body, embolic debris is not released from filter 110. Alternatively, after the filter 110 is magnetically coupled to catheter shaft 210, the catheter may be aspirated by providing a suction force to remove debris from the filter 110. The filter 110 may then be collapsed into catheter shaft 210 and catheter shaft 210 and filter 110 may be removed from the body.

Figure 25:
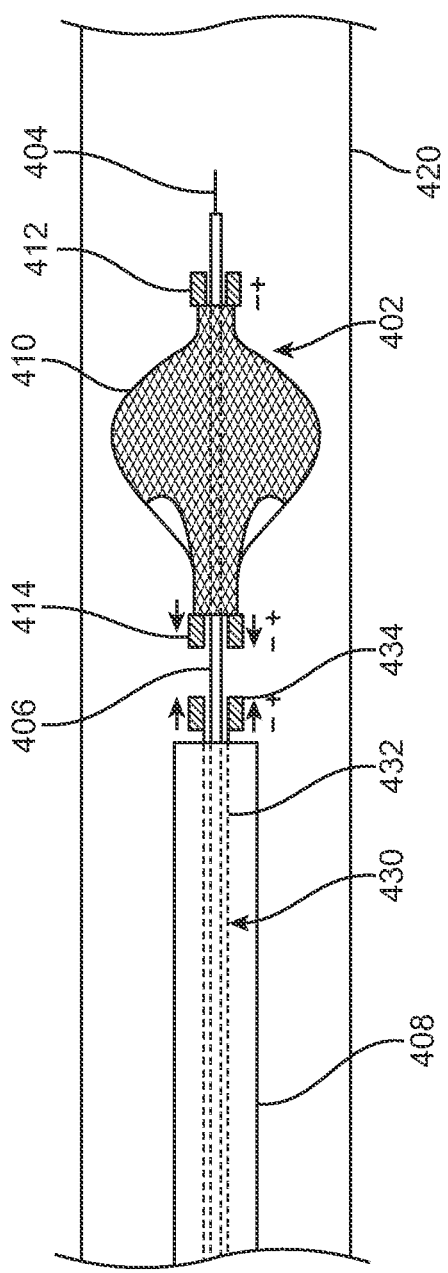
FIG. 25 is a schematic illustration of an embolic protection device utilizing magnets for deployment and retrieval thereof, and a method for deploying and retrieving the embolic protection device.

FIGS. 23-25 schematically show an embodiment of an embolic protection device 400 for deployment within a vessel 420. Embolic protection device 400 includes a filter assembly 402, a distal tip 404, an inner shaft 406, and an outer shaft or sheath 408. Distal tip 404 may integral with inner shaft 406 or may be a distal end of a guidewire extending through a lumen of inner shaft 406. Filter assembly 402 includes a filter 410 having a distal end 411 coupled to a distal magnet 412 and a proximal end 413 coupled to a proximal magnet 414. Distal magnet 412 is coupled to inner shaft 406 such that distal magnet 412 does not slide relative to inner shaft 406. Proximal magnet 414 is slidably coupled to inner shaft 406 such that proximal magnet 414 can slide relative to inner shaft 406. Proximal magnet 414 and distal magnet 412 are oriented such that there is a magnetic attraction force between them, as indicated by the magnetic pole indications in FIG. 23.

Filter 410 may be any material suitable for use in a filter. For example, and not by way of limitation, stainless steel, nitinol, polymers, or other filaments may be used to form filter 410. As described in more detail below, filter 410 need not be a shape memory material due to the use of magnets 412, 414 to open and close filter 410.

As shown in FIG. 23, embolic protection device 400 is in a delivery or compressed configuration with sheath 408 extended over filter 410. The radial force from sheath 408 overcomes the magnetic attraction force between magnets 412, 414 such that filter 410 remains in the compressed configuration. When embolic protection device 400 is advanced to a desired deployment location within vessel 420, sheath 408 is retracted, as shown in FIG. 24. With sheath no longer applying radial pressure on filter 410, the magnetic attraction force between magnets 412, 414 cause proximal magnet 414 to slide towards distal magnet 412, thereby expanding filter 410, as shown in FIG. 24. Proximal magnet 414 stops moving towards distal magnet 412 when filter is deployed. Stopping filter 410 from expanding beyond a desired amount can be accomplished in several ways. In one embodiment, the magnetic attraction force between magnets 412, 414 is designed to be less than the radial force of vessel 420 such that vessel 420 stops expansion of filter 410. In another embodiment, design features of filter assembly 402 stop filter 410 from over-expanding. In one non-limiting example, a stop (not shown) is provided on inner shaft 406 to prevent proximal magnet 414 from sliding past a desired location. In another non-limiting example, forces from filter 410 prevent proximal magnet from sliding past a desired location of inner shaft 406. In another non-limiting example, filter assembly 402 is designed such that filter 410 is deployed when proximal magnet 414 reaches distal magnet 412 such that proximal magnet is allowed to slide all the way to distal magnet 412. Those skilled in the art would recognize other methods to assure the proper deployment size of filter 410.

After deployment of filter assembly 402, sheath may be removed and a procedure upstream of filter 410 may be performed. Filter 410 capture emboli flowing downstream of the procedure, as discussed above. When the procedure for which the embolic protection device 400 was utilized is completed, a retrieval device 420 is utilized to collapse filter assembly 402 from its radial expanded or deployed configuration to the radially compressed configuration. In an embodiment, retrieval device 430 includes a retrieval magnet 434 disposed at a distal end of a retrieval shaft 432, as shown in FIG. 25. Inner shaft 406 may be backloaded into retrieval shaft 432 and retrieval shaft 432 is advanced over inner shaft 406, as shown in FIG. 25. Retrieval magnet 434 is oriented such that there is a magnetic attraction force between retrieval magnet 434 and proximal magnet 414, as represented by the magnetic pole markings in FIG. 25. Retrieval magnet 434 is configured to apply a larger attraction force on proximal magnet 414 than the attraction force between proximal magnet 414 and distal magnet 412. Accordingly, when retrieval magnet 434 is advanced adjacent to proximal magnet 414, the attraction force therebetween magnetic couples retrieval magnet 434 and proximal magnet 414. Retraction of retrieval magnet 434 causes proximal magnet 414 to move proximally to radially compress filter 410, as shown in FIG. 25. As would be understood by those skilled in the art, retrieval magnet 434 and proximal magnet 414 may be coupled to each other or the attraction force between the two magnets may be sufficient such that advancing retrieval magnet adjacent proximal magnet 414 is sufficient to cause proximal magnet 414 to move towards retrieval magnet 434 to radially compress filter 410. Retrieval shaft 432 may be retraced proximally to capture radially compressed filter 410 into sheath 408 or a separate retrieval shaft (not shown). Sheath 408 or such a retrieval catheter may then be removed from the body.

FIGS. 26-28 show schematically an embolic protection device 500 and a method of deploying and retrieving embolic protection device 500. FIGS. 26-28 do not show embolic protection device 500 deployed within a vessel for clarity. However, it would be understood by those skilled in the art that embolic protection device 500 can be deployed within a vessel, such as vessel 420 shown schematically in FIGS. 23-25. Embolic protection device 500 includes a filter assembly 502, a distal tip 504, an inner shaft 506, and an outer shaft or sheath 508. Distal tip 504 may integral with inner shaft 506 or may be a distal end of a guidewire extending through a lumen of inner shaft 506. Filter assembly 502 includes a filter 510 having a distal end 511 coupled to a distal magnet 512, an intermediate portion 513 coupled to a proximal magnet 514, and a proximal portion 521 coupled to a proximal connector 522. Distal magnet 512 is coupled to inner shaft 506 such that distal magnet 512 does not slide relative to inner shaft 506. Proximal magnet 514 is slidably coupled to inner shaft 506 such that proximal magnet 514 can slide relative to inner shaft 506. Proximal magnet 514 and distal magnet 512 are oriented such that there is an attractive magnetic force therebetween, as indicated by the magnetic pole indications in FIG. 26. Proximal connector 522 is slidably coupled to inner shaft 506 such that proximal connector 522 can slide relative to inner shaft 506. A shaft 524 is coupled to proximal connector 522 and is slidable relative to inner shaft 506.

Filter 510 further includes a distal mesh of filter 516 and a proximal mesh or filter 518. In one embodiment, distal filter 516 is a fine mesh filter such as a filter having pores in the range of 10-100 microns and proximal filter 518 is a coarse mesh such as a filter having pores larger than 100 microns. However, as known to those skilled in the art different sizes may be utilized depending on the intended location of filter 510 and the type of procedure for which filter 510 is being utilized. Accordingly, distal end 511 of filter 510 is a distal end of distal filter 516 and proximal end 513 of filter 510 is a proximal end of proximal filter 518. Proximal and distal filters 518, 516 meet at an intermediate portion of filter 510, which generally coincides with a proximal end of distal filter 516 and a distal end of proximal filter 518, as shown in FIG. 26. Filter assembly 502 further includes support arms or tethers 520 extending from intermediate portion 526 of filter 510 to proximal connector 522, as shown in FIG. 26. Although only two support arms are shown in FIG. 26 due to the view used, those skilled in the art would appreciate that more support arms may be utilized. In particular, three or four support arms 520 are preferable. As shown in FIG. 26, proximal ends of support arms 520 are the proximal end 521 of filter assembly 502 and are coupled to proximal connector 522.

Filters 516, 518 may be any material suitable for use in a filter. For example, and not by way of limitation, stainless steel, nitinol, polymers, or other filaments may be used to form filters 516, 518. As described in more detail below, filter 510 need not be a shape memory material due to the use of magnets 512, 514 and slidable connector 522 to open and close filter 510.

As shown in FIG. 26, embolic protection device 500 is in a delivery or compressed configuration with sheath 508 extended over filter 510, and proximal magnet 514 spaced apart from distal magnet 512 such that proximal filter 518 and distal filter 516 are disposed longitudinally relative to each other, or end-to-end. In other words, as shown in FIG. 26, in the delivery configuration, proximal magnet 514 and proximal end 513 of proximal filter 518 are disposed proximal of intermediate portion 526 (i.e. proximal end distal filter 516). The radial force from sheath 508 overcomes the magnetic attraction force between magnets 512, 514 such that filter 510 remains in the delivery configuration.

When embolic protection device 500 is advanced to a desired deployment location within a vessel, sheath 508 is retracted, as shown in FIG. 27. With sheath 508 no longer applying radial pressure on filter 510, the magnetic attraction force between magnets 512, 514 causes proximal magnet 514 to slide towards distal magnet 512, thereby expanding filter 510, as shown in FIG. 27. Proximal magnet 514 stops moving towards distal magnet 512 when filter 510 is deployed. Stopping filter 510 from expanding beyond a desired amount can be accomplished in several ways. In one embodiment, the magnetic attraction force between magnets 512, 514 is designed to be less than the radial force of the vessel such that the vessel stops expansion of filter 510. In another embodiment, design features of filter assembly 502 stop expansion of filter 510. In one non-limiting example, a stop (not shown) is provided on inner shaft 506 to prevent proximal magnet 514 or proximal connector 522 from sliding past a desired location. In another non-limiting example, forces from filter 510 prevent proximal magnet 514 from sliding past a desired location of inner shaft 506. Those skilled in the art would recognize other methods to assure the proper deployment size of filter 510.

After filter assembly 502 is deployed, sheath 508 may be removed (not shown) and a procedure upstream of filter 510 may be performed. With filter assembly 502 deployed as shown in FIG. 27, blood flow through the vessel passes through proximal (coarse mesh) filter 518 and then distal (fine mesh) filter 516. Accordingly, large emboli are captured by proximal filter 518 and smaller emboli are captured by distal filter 516.

When the procedure for which the embolic protection device 500 was utilized is completed, filter assembly 502 is radially compressed into a retrieval configuration, shown in FIG. 28. Filter assembly 502 is radially compressed by pulling shaft 524, which is coupled to slidable connector 522. Because of the magnetic attraction between magnets 512, 514, retraction of shaft 524 does not cause proximal magnet 514 to slide proximally. Instead, as shown in FIG. 27, intermediate portion 526 of filter 510, where distal filter 516 and proximal filter 518 meet, is pulled proximally and towards inner shaft 506 by support arms 520. This movement captures the emboli within filter 510 as distal (fine mesh) filter 516 provides a distal block and a proximal block to prevent emboli from escaping filter 510. Filter assembly 502 may then be pulled into sheath 508 or a separate recapture sheath, or sheath 508 or a separate recapture sheath may be pushed distally over filter assembly 502.

FIGS. 29-31 show schematically an embolic protection device 600 and a method of deploying and retrieving embolic protection device 600. FIGS. 29-31 do not show embolic protection device 600 deployed within a vessel for clarity. However, it would be understood by those skilled in the art that embolic protection device 600 can be deployed within a vessel, such as vessel 420 shown schematically in FIGS. 23-25. Embolic protection device 600 includes a filter assembly 602, a distal tip 604, an inner shaft 606, and an outer shaft or sheath 608. Distal tip 604 may be integral with inner shaft 606 or may be a distal end of a guidewire extending through a lumen of inner shaft 606. Similar to filter assembly 502, filter assembly 602 includes a filter 610 having a distal end 611 coupled to a distal magnet 612, an intermediate portion 613 coupled to a proximal magnet 614, and a proximal portion 621 coupled to a proximal connector 622. Distal magnet 612 is coupled to inner shaft 606 such that distal magnet 612 does not slide relative to inner shaft 606. Proximal magnet 614 is slidably coupled to inner shaft 606 such that proximal magnet 614 can slide relative to inner shaft 606. Proximal magnet 614 and distal magnet 612 are oriented such that there is a repulsive magnetic force therebetween, as indicated by the magnetic pole indications in FIG. 29. Proximal connector 622 is slidably coupled to inner shaft 606 such that proximal connector 622 can slide relative to inner shaft 606. A shaft 624 is coupled to proximal connector 622 and is slidable relative to inner shaft 606.

Filter 610 further includes a distal mesh of filter 616 and a proximal mesh or filter 618. In one embodiment, distal filter 616 is a fine mesh filter such as a filter having pores in the range of 10-100 microns and proximal filter 618 is a coarse mesh such as a filter having pores larger than 100 microns. However, as known to those skilled in the art different sizes may be utilized depending on the intended location of filter 610 and the type of procedure for which filter 610 is being utilized. Accordingly, distal end 611 of filter 610 is a distal end of distal filter 616 and proximal end 613 of filter 610 is a proximal end of proximal filter 618. Proximal and distal filters 618, 616 meet at an intermediate portion 626 of filter 610, which generally coincides with a proximal end of distal filter 616 and a distal end of proximal filter 618, as shown in FIG. 30. Filter assembly 602 further includes support arms or tethers 620 extending from intermediate portion 626 of filter 610 to proximal connector 622, as shown in FIGS. 29-31. Although only two support arms are shown in the figures due to the view used, those skilled in the art would appreciate that more support arms may be utilized. In particular, three or four support arms 620 are preferable. As shown in FIGS. 29-31, proximal ends of support arms 620 are the proximal end 621 of filter assembly 602 and are coupled to proximal connector 622.

Filters 616, 618 may be any material suitable for use in a filter. For example, and not by way of limitation, stainless steel, nitinol, polymers, or other filaments may be used to form filters 616, 618. As described in more detail below, filter 610 need not be a shape memory material due to the use of magnets 612, 614 and slidable connector 622 to open and close filter 610.

As noted above, embolic protection device 600 is similar to embolic protection device 500 of FIGS. 26-28. However, as shown in FIG. 26, embolic protection device 600 in a delivery or radially compressed configuration with sheath 608 extended over filter 610, proximal magnet 614 is disposed nearer to distal magnet 612 than intermediate portion 626 is to distal magnet 612. Accordingly, the delivery configuration of embolic protection device 600 is different from the delivery configuration of embolic protection device 500. Further, as noted above, proximal and distal magnets 614, 612 as oriented such that there is a repulsive magnetic force therebetween. Accordingly, in the delivery configuration of FIG. 29, radial force from sheath 608 overcomes the repulsive magnetic force between magnets 612, 614 such that filter 610 remains in the delivery configuration.

When embolic protection device 600 is advanced to a desired deployment location within a vessel, sheath 608 is retracted, as shown in FIG. 30. With sheath 608 no longer applying radial pressure on filter 610, the repulsive magnetic force between magnets 612, 614 (as indicated by arrows A) causes proximal magnet 614 to slide away from distal magnet 612, thereby expanding filter 610, as shown in FIG. 30. Proximal connection 622 also moves towards distal magnet 612 as filter 610 radially expands (as indicated by arrow B). Proximal magnet 614 stops moving away from distal magnet 612 when filter 610 is deployed. Stopping proximal magnet 614 from moving away from distal magnet 612 beyond a desired amount can be accomplished in several ways. In one embodiment, the repulsive magnetic force between magnets 612, 614 is designed to be less than the radial force of the vessel such that the vessel stops expansion of filter 610. In another embodiment, design features of filter assembly 602 and the amount of the repulsive magnetic force stop expansion of filter 610. In one non-limiting example, the repulsive magnetic force between magnets 612, 614 is such that when proximal magnet 614 reaches a certain distance away from distal magnet 612, the repulsive force is no longer large enough to cause proximal magnet 614 to move. In another non-limiting example, a stop (not shown) is provided on inner shaft 606 to prevent proximal magnet 614 or proximal connector 622 from sliding past a desired location. In another non-limiting example, forces from filter 610 prevent proximal magnet 614 from sliding past a desired location of inner shaft 606. Those skilled in the art would recognize other methods to assure the proper deployment size of filter 610.

After filter assembly 602 is deployed, sheath 608 may be removed (not shown) and a procedure upstream of filter 610 may be performed. With filter assembly 602 deployed as shown in FIG. 30, blood flow through the vessel passes through proximal (coarse mesh) filter 618 and then distal (fine mesh) filter 616. Accordingly, large emboli are captured by proximal filter 618 and smaller emboli that pass through proximal filter 618 are captured by distal filter 616.

When the procedure for which the embolic protection device 600 was utilized is completed, filter assembly 602 is radially compressed into a retrieval configuration, shown in FIG. 31. Filter assembly 602 is radially compressed by pulling shaft 624, which is coupled to slidable connector 622. This pulling force overcomes the repulsive magnetic force between proximal and distal magnets 614, 612 magnets such that proximal connection 622 moves proximally as indicated by arrow C and proximal magnet 614 moves distally as indicated by arrow D, as shown in FIG. 31. As also shown in FIG. 31, intermediate portion 626 moves proximally and towards inner shaft 606 to radially compress filter 610. Filter assembly 602 may then be pulled into sheath 608 or a separate recapture sheath, or sheath 608 or a separate recapture sheath may be pushed distally over filter assembly 602.

FIGS. 32-34 show schematically an embolic protection device 700 and a method of deploying and retrieving embolic protection device 700. FIGS. 32-34 do not show embolic protection device 700 deployed within a vessel for clarity. However, it would be understood by those skilled in the art that embolic protection device 700 can be deployed within a vessel, such as vessel 420 shown schematically in FIGS. 23-25. Embolic protection device 700 includes a filter assembly 702, a distal tip 704, an inner shaft 706, and an outer shaft or sheath 708. Distal tip 704 may be integral with inner shaft 706 or may be a distal end of a guidewire extending through a lumen of inner shaft 706.

Filter assembly 702 includes a filter 710 having a distal end 711 coupled to a distal magnet 712 and a proximal end 717 coupled to a proximal magnet 718. Distal magnet 712 is coupled to inner shaft 706 such that distal magnet 712 does not slide relative to inner shaft 706. Proximal magnet 718 is slidably coupled to inner shaft 706 such that proximal magnet 718 can slide relative to inner shaft 706. Filter assembly further includes two intermediate magnets 714, 716 disposed between proximal magnet 718 and distal magnet 712. Intermediate magnets 714, 716 are coupled to inner shaft 706 such that intermediate magnets 714, 716 can slide relative to inner shaft 706. A first flexible shaft or bellows 720 is disposed between distal magnet 712 and intermediate magnet 714. A second flexible shaft or bellow 722 is disposed between intermediate magnet 714 and intermediate magnet 716, and a third flexible shaft or bellows 724 is disposed between intermediate magnet 716 and proximal magnet 718, as shown in FIG. 33. Bellows 720, 722, 724 are disposed around inner shaft 706 such that there are annular or inflations lumens 721, 723, 725 between inner shaft 706 and each of the bellows 720, 722, 724. Further, magnets 714, 716, 718 are coupled to inner shaft 706 such that a lumen extends through magnets 714, 716, 718 between inner shaft 706 and each magnet 714, 716, 718. Further, a shaft 726 disposed around inner shaft 706 extends proximally from proximal magnet 718 to a proximal end of embolic protection device 700. An annular or inflation lumen 728 is disposed between inner shaft 706 and shaft 726. Inflation lumen 728 is fluidly connected to inflation lumens 721, 723, 725. Distal magnet 712 is coupled to inner shaft 706 such that fluid from inflation lumen 721 cannot pass therethrough.

Magnets 712, 714, 716, 718 are oriented such that there is an attractive magnetic force between proximal magnet 718 and intermediate magnet 716, between intermediate magnet 716 and intermediate magnet 714, and between intermediate magnet 714 and distal magnet 712, as indicated by the magnetic pole indications in FIG. 32.

Filter 710 as shown in FIGS. 32-34 is a single mesh filter. However, those skilled in the art would recognize that a dual mesh filter, such as the filters described with respect to 26-28 and 29-31 could also be used with the embolic protection device 700 of FIGS. 32-34. Filter 710 may be a mesh filter having pores in the range of 10-400 microns. However, as known to those skilled in the art different sizes may be utilized depending on the intended location of filter 710 and the type of procedure for which filter 710 is being utilized. Filter 710 may be any material suitable for use in a filter. For example, and not by way of limitation, stainless steel, nitinol, polymers, or other filaments may be used to form filter 710. As described in more detail below, filter 710 need not be a shape memory material due to the use of magnets 712, 714, 716, 718 and bellows 720, 722, 724 to open and close filter 710.

As shown in FIG. 32, embolic protection device 700 is in a delivery or radially compressed configuration with sheath 708 extended over filter 710. As shown in FIG. 32, magnets 712, 714, 716, 718 are spaced from each other and bellows 720, 722, 724 are in a straightened configuration. Although this configuration the bellows are described as "straightened", the term as used herein means that the bellows 720, 722, 724 are straighter than the configuration described below with respect to FIG. 33, wherein filter 710 is radially expanded. Further, magnets 712, 714, 716, 718 are described as spaced from each other in the radially compressed or delivery configuration of filter 710. As used herein, the magnets 712, 714, 716, 718 are spaced a first distance from each other that is greater than the distance that they are spaced from each other when filter 710 is in the radially expanded or deployed configuration of FIG. 33. In FIG. 32, the radially force of sheath 708 on filter 710 overcomes the magnetic attraction force between magnets 712, 714, 716, 718 to keep magnets 712, 714, 716, 718 spaced relative to each other and filter 710 in the radially compressed or delivery configuration.

When embolic protection device 700 is advanced to a desired deployment location within a vessel, sheath 708 is retracted, as shown in FIG. 33. With sheath 708 no longer applying radial pressure on filter 710, the attractive magnetic force between magnets 712, 714, 716, 718 causes intermediate magnet 714 to slide towards distal magnet 712, intermediate magnet 716 to slide towards intermediate magnet 714, an proximal magnet 718 to slide towards intermediate magnet 716, thereby expanding filter 710, as shown in FIG. 33. Stopping magnets 714, 716, 718 so that they move distally a desired amount can be accomplished in several ways. In a non-limiting embodiment, the attractive magnetic force between magnets 712, 714, 716, 718 is designed to be less than the radial force of the vessel such that the vessel stops expansion of filter 710. In another non-limiting embodiment, as bellows 720, 722, 724 are longitudinally compressed, each applies a force resisting the movement of intermediate magnet 714 towards distal magnet 712, intermediate magnet 716 towards intermediate magnet 714, and proximal magnet 718 towards intermediate magnet 716, respectively. In another non-limiting embodiment, stops (not shown) may be provided on inner shaft 706 to prevent movement of magnets 714, 716, 718 beyond a desired point. In another non-limiting example, other forces of filter assembly 702 prevent magnets 714, 716, 718 from sliding past a desired location of inner shaft 706. Those skilled in the art would recognize other methods to assure the proper deployment size of filter 710.

After filter assembly 702 is deployed, sheath 708 may be removed (not shown) and a procedure upstream of filter 710 may be performed. With filter assembly 702 deployed as shown in FIG. 33, blood flow through the vessel passes through filter 710 and emboli are captured by filter 710.

When the procedure for which the embolic protection device 700 was utilized is completed, filter assembly 702 is radially compressed into a retrieval configuration, shown in FIG. 34. Filter assembly 702 is radially compressed by injecting a fluid, such as saline, into annular lumen 728. Such a fluid is injected into annular lumen 728 at a proximal end of embolic protection device (not shown) through an inflation port (not shown). Such inflation ports at proximal ends of catheters are well known to those skilled in the art, for example, as used in balloon catheters. As the fluid is injected into annular lumen 728, the fluid continues distally to lumens 721, 723, and 725 described above. When the lumens are filled and pressure continues to build, bellows 720, 722, 724 expand longitudinally. This longitudinal expansion of bellows 720, 722, 724 overcomes the magnetic attraction force between magnets 712, 714, 716, 718 such that intermediate magnet 714 moves away from distal magnet 712, intermediate magnet 716 moves away from intermediate magnet 714, and proximal magnet 718 moves away from intermediate magnet 716, as shown in FIG. 34. This movement causes proximal end 717 of filter 710 to move away from distal end 711 of filter 710, thereby radially compressing filter 710, as shown in FIG. 34. Filter assembly 702 may then be pulled into sheath 708 or a separate recapture sheath, or sheath 708 or a separate recapture sheath may be pushed distally over filter assembly 702.

While FIGS. 32-34 show four magnets 712, 714, 716, 718 with three bellows 720, 722, 724 disposed therebetween, those skilled in the art would recognize that more or less magnets and bellows may be used.

FIGS. 35-37 show schematically an embolic protection device 800 and a method of deploying and retrieving embolic protection device 800. FIGS. 35-37 do not show embolic protection device 800 deployed within a vessel for clarity. However, it would be understood by those skilled in the art that embolic protection device 800 can be deployed within a vessel, such as vessel 420 shown schematically in FIGS. 23-25. Embolic protection device 800 includes a filter assembly 802, a distal tip 804, an inner shaft 806, and an outer shaft or sheath 808. Distal tip 804 may be integral with inner shaft 806 or may be a distal end of a guidewire extending through a lumen of inner shaft 806. Filter assembly 802 includes a filter 810 having a distal end 811 coupled to inner shaft 806 at a distal connection 812 and a proximal end 813 to inner shaft 806 at a proximal connector 814. Distal connection 812 is coupled to inner shaft 806 such that distal connection 812 does not slide relative to inner shaft 806. Proximal connection is slidably coupled to inner shaft 806 such that proximal connection 814 can slide relative to inner shaft 806. A shaft 824 is coupled to proximal connector 822 and is slidable relative to inner shaft 806.

Filter assembly 802 further includes magnets 816, 818 disposed on a first side of filter 810 and magnets 820, 822 disposed on an opposing side of filter 810. Magnets 816, 818, 820, 822 are oriented such that there is an repulsive magnetic force between magnets 816 and 820 and a repulsive magnetic force between magnets 818 and 822, as indicated by the magnetic pole indications in FIG. 35.

Filter 810 as shown in FIGS. 35-37 is a single mesh filter. However, those skilled in the art would recognize that a dual mesh filter, such as the filters described with respect to FIGS. 26-28 and 29-31 could also be used with the embolic protection device 800 of FIGS. 35-37. Filter 810 may be a mesh filter having pores in the range of 10-400 microns. However, as known to those skilled in the art different sizes may be utilized depending on the intended location of filter 810 and the type of procedure for which filter 810 is being utilized. Filter 810 may be any material suitable for use in a filter. For example, and not by way of limitation, stainless steel, nitinol, polymers, or other filaments may be used to form filter 810. As described in more detail below, filter 810 need not be a shape memory material due to the use of magnets 816, 818, 820, 822 to open filter 810.

Embolic protection device 800 is shown in FIG. 35 in a delivery or radially compressed configuration with sheath 808 extended over filter 810 and proximal connection 814 is disposed relatively spaced apart from distal connection 812. A radially inward force from sheath 808 overcomes the repulsive magnetic force between magnets 816, 820 and magnets 818, 822 such that filter 810 remains in the delivery configuration shown in FIG. 35.

When embolic protection device 800 is advanced to a desired deployment location within a vessel, sheath 808 is retracted, as shown in FIG. 36. With sheath 808 no longer applying radial force on filter 810, the repulsive magnetic force between magnets 816, 820 and 818, 822 (as indicated by arrows A) causes opposing sides of filter 810 to move away from each other, as shown in FIG. 36. As opposing sides of filter 810 move away from each other, proximal connection 814 slides towards distal connection 812, as also shown in FIG. 36. These movements result in the radially expanded or deployed configuration shown in FIG. 36. The repulsive magnetic force between magnets 816, 820 and magnets 818, 822 ensures that filter 810 is firmly planted against the vessel wall so that emboli do not escape around filter 810 when deployed as described below. Ensuring that magnets 816, 820 and magnets 818, 820 separate by the desired amount can be accomplished in several ways. In one embodiment, the repulsive magnetic force between magnets 816, 820 and magnets 818, 822 is designed to be less than the radial force of the vessel such that the vessel stops expansion of filter 810. In another embodiment, design features of filter assembly 802 and the amount of the repulsive magnetic force stop expansion of filter 810. In one non-limiting example, the repulsive magnetic force between magnets 816, 820 and magnets 818, 822 is such that when magnets 816, 818 reach a certain distance away from magnets 820, 822, respectively, the repulsive force is no longer large enough to cause the magnets to separate. In another non-limiting example, a stop (not shown) is provided on inner shaft 806 to prevent proximal connector 814 from sliding past a desired location. In another non-limiting example, forces from filter assembly 802 prevent expansion of filter 810 beyond a desired amount. Those skilled in the art would recognize other methods to assure the proper deployment size of filter 810.

After filter assembly 802 is deployed, sheath 808 may be removed (not shown) and a procedure upstream of filter 810 may be performed. With filter assembly 802 deployed as shown in FIG. 36, blood flow through the vessel passes through filter 810, which captures emboli in the bloodstream.

When the procedure for which the embolic protection device 800 was utilized is completed, filter assembly 802 is radially compressed into a retrieval configuration, shown in FIG. 37. Filter assembly 802 is radially compressed by pulling shaft 824, which is coupled to slidable proximal connector 814. This pulling force overcomes the repulsive magnetic force between magnets 816, 820 and the repulsive magnetic force between magnets 818, 822 such that proximal connection 814 moves proximally as indicated by arrow B, as shown in FIG. 37. Filter assembly 802 may then be pulled into sheath 808 or a separate recapture sheath, or sheath 808 or a separate recapture sheath may be pushed distally over filter assembly 802.

Although proximal and distal connections 814, 812 in FIGS. 35-37 have not been described as magnets, those of ordinary skill in the art would recognize that proximal and distal connections 814, 812 may be proximal and distal magnets such as those described with respect to FIGS. 23-25. Thus, in addition to the repulsive magnetic force between magnets 816, 820 and the repulsive magnetic force between magnets 818, 822, an attractive magnetic force between proximal connection 814 and distal connection 812 would slide proximal connection 814 towards distal connection 812. Accordingly, with such a variation, a magnet could be used to convert filter 810 from the radially expanded or deployed configuration of FIG. 36 to the radially compressed configuration of FIG. 37, as explained above with respect to FIG. 25.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. It will also be understood that each feature of each embodiment discussed herein, and of each reference cited herein, can be used in combination with the features of any other embodiment. Further, while the embodiment described above have referred to magnets, the term as used herein refers to permanent magnets and magnetized materials. All patents and publications discussed herein are incorporated by reference herein in their entirety.

What is claimed is:

1. An embolic protection device comprising:
an inner shaft;
a filter mesh having a first end fixedly coupled to the inner shaft and a second end slidably coupled to the inner shaft;
a first magnet attached to the filter mesh to a first side of the inner shaft; and
a second magnet attached to the filter mesh to a second side of the inner shaft opposite the first side of the inner shaft,
wherein the first magnet and the second magnet are oriented to magnetically repel each other such the filter radially expands.

2. The embolic protection device of claim 1, wherein the first magnet comprises a first plurality of magnets and the second magnet comprises a second plurality of magnets.

3. The embolic protection device of claim 1, wherein the filter mesh includes a radially compressed configuration, and wherein with the filter mesh in the radially compressed configuration the first magnet and the second magnet are oriented to magnetically repel each other to transition the filter mesh to a radially expanded configuration.

4. The embolic protection device of claim 3, further comprising an outer shaft disposed around the filter mesh with the filter mesh in the radially compressed configuration, wherein the outer shaft is configured to provide a radial force preventing the filter mesh from expanding to the radially expanded configuration.

5. The embolic protection device of claim 1, further comprising a shaft coupled to the second end of the filter mesh, the shaft being slidably disposed over the inner shaft and configured to provide a pull force on the second end of the filter mesh to transition the filter mesh from the radially expanded configuration to a retrieval configuration.

6. The embolic protection device of claim 1, wherein the first end of the filter mesh is fixedly coupled to the inner shaft at a distal connector, and wherein the second end of the filter mesh is slidably coupled to the inner shaft at a proximal connector.

7. The embolic protection device of claim 6, wherein the distal connector and the proximal connector are each a magnet.

8. The embolic protection device of claim 7, wherein the distal connector and the proximal connector are oriented such that the distal connector and the proximal connector are magnetically attracted to each other.

9. The embolic protection device of claim 1, wherein the filter mesh is a single filter mesh.

10. The embolic protection device of claim 1, wherein the filter mesh is a dual filter mesh.

11. The embolic protection device of claim 1, wherein the filter mesh includes a plurality of pores, wherein a pore size of each of the plurality of pores is in the range of 10-400 microns.

* * * * *